United States Patent [19]

MacLeay et al.

[11] 4,219,476
[45] Aug. 26, 1980

[54] TERTIARY ALIPHATIC AMIDAZO COMPOUND

[75] Inventors: Ronald E. MacLeay, Williamsville; Chester S. Sheppard, Kenmore, both of N.Y.

[73] Assignee: Pennwalt Corporation, Philadelphia, Pa.

[21] Appl. No.: 686,603

[22] Filed: May 14, 1976

Related U.S. Application Data

[60] Division of Ser. No. 148,885, Jun. 1, 1971, Pat. No. 4,001,207, which is a division of Ser. No. 725,180, Apr. 29, 1968, abandoned, which is a continuation-in-part of Ser. No. 616,158, Feb. 15, 1967, abandoned, which is a continuation-in-part of Ser. No. 409,306, Nov. 5, 1964, abandoned.

[51] Int. Cl.² .................. C07C 107/02; C07C 107/06; C08F 4/04
[52] U.S. Cl. .................................. 260/192; 260/152; 260/157; 260/158; 526/219
[58] Field of Search ............... 260/192, 152, 157, 158

[56] References Cited

PUBLICATIONS

Andrisano et al., Chemical Abstracts, vol. 59, p. 9468 and 9469 (1963).
Neighbors et al., J. Am. Chem. Soc., vol. 44, pp. 1557 to 1564 (1922).
Straneo, Chemical Abstracts, vol. 35, p. 5473 (1941).

*Primary Examiner*—Floyd D. Higel

[57] ABSTRACT

An unsymmetrical azo compound having the formula

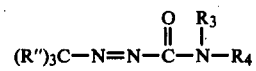

is provided wherein R'' is an alkyl or aralkyl and $R_3$ and $R_4$ are hydrogen or aliphatic. The compound is useful as a vinyl polymerization initiator, a polyester resin curing agent and a blowing agent for foamed plastics.

3 Claims, No Drawings

TERTIARY ALIPHATIC AMIDAZO COMPOUND

This application is a division of application Ser. No. 148,885, filed June 1, 1971, now U.S. Pat. No. 4,001,207, which in turn is a division of application Ser. No. 725,180, filed Apr. 29, 1968, now abandoned, which is a continuation-in-part of application Ser. No. 616,158 filed Feb. 15, 1967, now abandoned, which is a continuation-in-part of application Ser. No. 409,306, filed Nov. 5, 1964, now abandoned.

BACKGROUND OF THE INVENTION

This invention relates to unsymmetrical azo compounds, unsymmetrical hydrazo compounds, processes for preparing these compounds and processes utilizing these compounds, which azo and hydrazo compounds are characterized by having a tertiary carbon atom joined to one of the azo or hydrazo nitrogens.

Symmetrical azo compounds having a tert-carbon atom joined to each azo nitrogen are known:
T. E. Stevens, J. Org. Chem. 26, 2531 (1961).
E. Farenhorst and E. C. Kooyman, Rec. Trav. Chim. 72, 993 (1953).
S. F. Nelson and P. D. Bartlett, J. Am. Chem. Soc. 88, 137, 143 (1966).

Unsymmetrical azo compounds where a tert-carbon atom is joined to one azo nitrogen are known. Illustrative compounds of this type, none coming within the scope of the invention are given in:
M. C. Chaco and N. Rabjohn, J. Org. Chem. 27, 2765 (1962).
D. C. Iffland, L. Salisbury, and W. R. Schafer, J. Am. Chem. Soc. 83, 747 (1961).
D. Y. Curtin and J. A. Ursprung, J. Org. Chem. 21, 1221 (1956).
C. G. Overberger and A. V. Di Giulio, J. Am. Chem. Soc. 80, 6562 (1958); ibid 81, 2154 (1959).
H. Wieland, et al, Ann. 514, 145 (1934).

The above compounds are in general difficult to prepare, or are so stable that they are not useful as free radical generators or as blowing agents for plastic foams.

2,2'-azobisisobutyronitrile is commercially available. This compound has the structure $$CH_3-\underset{\underset{CN}{|}}{\overset{\overset{CH_3}{|}}{C}}-N=N-\underset{\underset{CN}{|}}{\overset{\overset{CH_3}{|}}{C}}-CH_3 \quad \text{IXA}$$

It has many shortcomings. It is a toxic solid. Moreover, the decomposition residue is a highly toxic solid. Thus, it presents a toxic dusting problem when used in commercial operations and extreme precautions are required in its handling. It is not used in many applications for which it is suited because other areas at the manufacturing site cannot tolerate even the remote chance of exposure to such toxic dust. This is especially true when manufacturing goods for the food and drug packaging industries and many other goods for the household consumer. It cannot be used as a blowing agent for the great majority of the plastic foam market due to the high levels of the toxic residue left in the foamed product. It is insoluble in petroleum hydrocarbon solvents and possesses very low or limited solubility in most of the organic common solvents such as aromatic hydrocarbons, dioxane, alcohol, ether and carbon tetrachloride. This insoluble nature eliminates its use for many applications for which it would otherwise be suitable. It presents problems of metering, incorporation, mixing, dispersing, etc. and necessitates the use of a solvent that in many cases is not ideally suited for the particular application.

The new compositions of the present invention eliminate these problems. Most of the new compositions are liquids and are soluble in petroleum hydrocarbon and most of the other common organic solvents. Thus, no dusting, metering, incorporating, mixing, and dispersing problems are encountered in using these new compositions. Also the new compositions and their decomposition residues have chemical structures that suggest that they are, for the most part, significantly less toxic. Preliminary toxicological studies on the new compositions made in Examples I and II, set out later, and the decomposition residue of the Example I product indicate that they are significantly less toxic than IXA and its decomposition residue. The less toxic nature of the new compositions coupled with their liquid and high solubility properties allows them to be used in many applications where IXA cannot be used.

Unsymmetrical tert-carbon containing hydrazo compounds are known. Illustrative literature showing the prior art types of these compounds is presented:
Thiele, B. 28, 2600.
Angeli, Rome Atti Accad Tincei 26 I, 95 (1917).
Thiele and Strange, Ann 283, 33 (1894)
D. Neighbors et al., J. Am. Chem. Soc. 44, 1557 (1922).

SUMMARY OF THE INVENTION

1. Novel azo compounds $$R''-\underset{\underset{R''}{|}}{\overset{\overset{R''}{|}}{C}}-N=N-R' \qquad \text{I.}$$

where:
(1) R'' is a lower alkyl of 1–13 carbons, aralkyl such as benzyl or phenethyl or phenyl radical and not more than one phenyl may be present;
(2) R' is one of the following radicals:

$$-\underset{\underset{Z}{|}}{\overset{\overset{R_1}{|}}{C}}-R_2, \quad -\overset{\overset{O}{\|}}{C}-\underset{}{\overset{\overset{R_3}{|}}{N}}-R_4, \quad -\overset{\overset{O}{\|}}{C}-R_5, \quad -\underset{\underset{R_8}{|}}{\overset{\overset{-C-R_6}{\|}}{C}}-R_7,$$

$$-\overset{\overset{N}{\|}}{C}\underset{\underset{N}{\diagdown}}{\diagup}Z', \text{ and } -R_{12}-N=N-C(R'')_3$$

where:
(a) $R_1$ and $R_2$ are lower aliphatic or cycloaliphatic radicals and together may form an alkylene biradical, and $R_2$ may also be phenyl or a substituted phenyl;
(b) $R_3$ and $R_4$ are hydrogen, lower aliphatic such as alkyl of 1–20 carbons, or cycloaliphatic radicals such as cycloalkyl of 3–6 carbons and together may form an alkylene biradical of 2–16 carbons; $R_3$ and $R_4$ may also be selected from an alkyl of 1–20 carbons containing a carboxy or methoxycarbonyl substituent.
(c) $R_5$ is a lower aliphatic, cycloaliphatic or aromatic radical;

(d) $R_6$ is a lower alkyl radical;
(e) $R_7$ and $R_8$ are hydrogen or lower alkyl radicals;
(f) $R_6$ and $R_7$ together may form an alkylene biradical;
(g) $Z'$ is a zero, mono-, or di- valent remainder of a heterocyclic ring;

(h) Z is a radical:

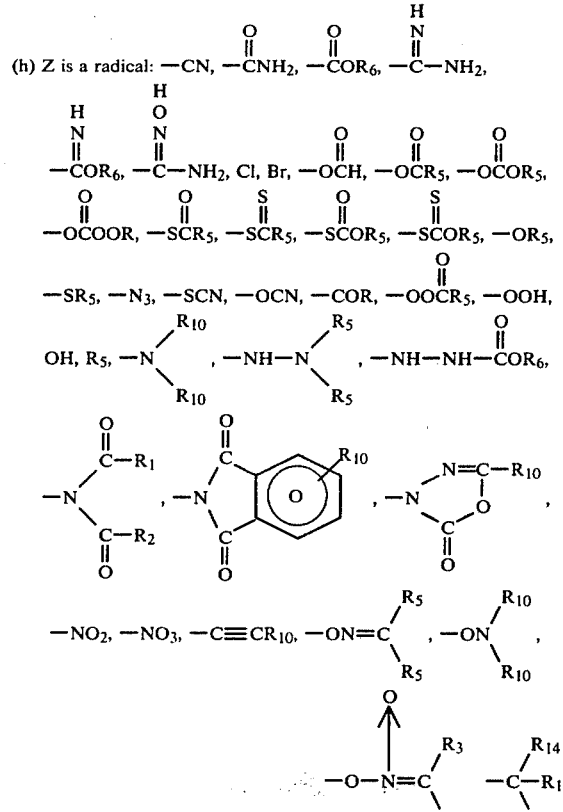

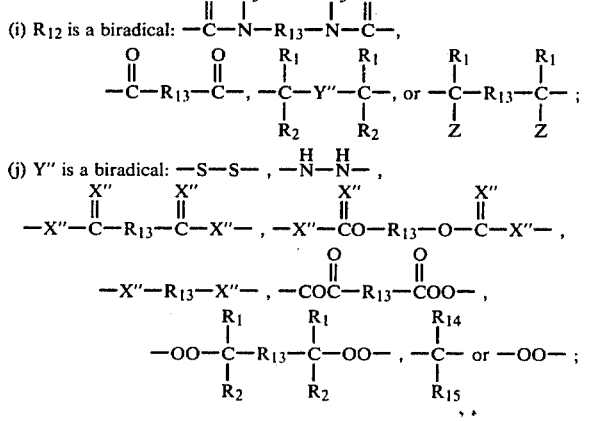

(i) $R_{12}$ is a biradical:

(j) $Y''$ is a biradical:

(k) $R_{13}$ is an aliphatic, cycloaliphatic, or aromatic biradical;
(l) $X''$ is oxygen or sulfur;
(m) $R_{10}$ is hydrogen, lower aliphatic, cycloaliphatic, or aromatic;

(n) $R_{14}$ and $R_{15}$ are

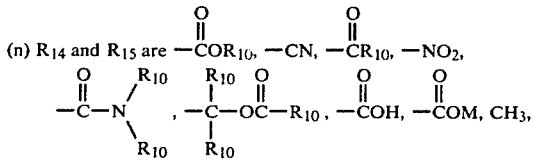

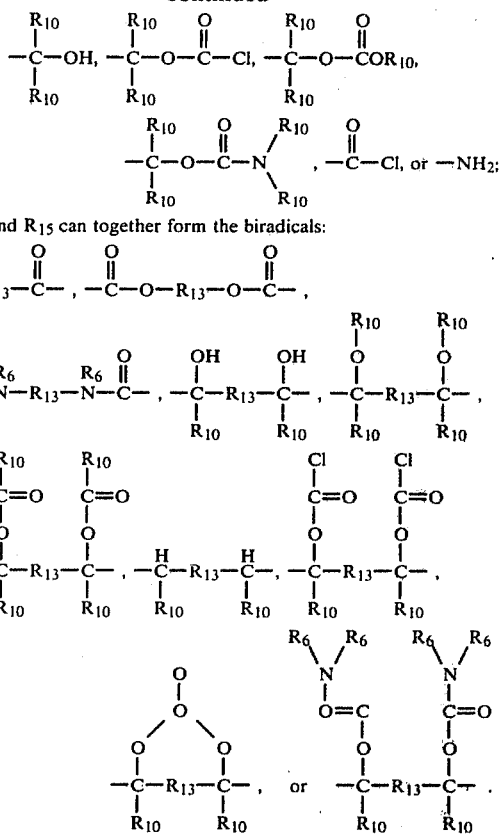

(o) $R_{14}$ and $R_{15}$ can together form the biradicals:

2. Novel hydrazo compounds

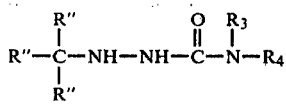
II.

where:
(a) $R''$ is a lower alkyl, aralkyl or phenyl radical and not more than one phenyl is present; and
(b) $R_3$ and $R_4$ are hydrogen, lower aliphatic or cycloaliphatic radicals and together may form an alkylene biradical.

3. First process: Preparation of cyanoazo compounds.
A. General Procedure for All Ketones
(1) Reacting $R-NH-NH_2$ and

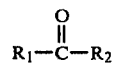

in the presence of an inert solvent while removing the water produced substantially continuously during the reaction to form

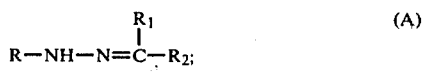
(A)

(2) reacting A with hydrogen cyanide at a temperature from about 10° C. to 80° C. to form

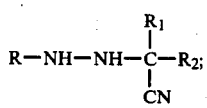 (B)

and (3) oxidizing B to form the desired azo product

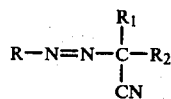 (C)

where:

(a) R is the radical

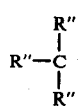

with R" being a lower alkyl, aralkyl or phenyl radical and not more than one phenyl is present; and (b) $R_1$ and $R_2$ are lower aliphatic or cycloaliphatic radicals and together may form an alkylene biradical.

B. General Procedure for water soluble and partially soluble ketones.

Reacting the R—NHNH$_2$ acid salt with MCN and $R_1$—C(O)—$R_2$ in water to form [B] above and oxidizing [B] to form the corresponding azo product.

4. Second process: Preparation of α-haloazo compounds.

Reacting (A) and halogen (Cl$_2$, Br$_2$, or I$_2$) to form the α-haloazo product

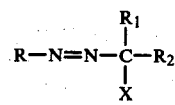

(P) where:

(a) R is the radical (R")$_3$C— with R" being a lower alkyl, aralkyl or phenyl radical and not more than one phenyl is present;

(b) $R_1$ and $R_2$ are lower aliphatic or cycloaliphatic radicals and together may form an alkylene biradical, and $R_1$ may also be phenyl or substituted phenyl; and (c) X is chlorine, bromine, or iodine.

5. Third process: Preparation of α-substituted-azo compounds.

Reacting

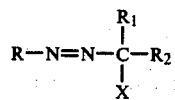

and MY, MY" or MY"H or (MY"E, YH, HY"H in the presence of a base) to form the α-substituted-azo product

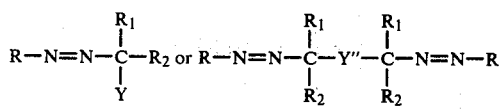 (Q)

where: R, $R_1$, $R_2$, and X are defined as above and
(a) M is an alkali or alkaline earth metal;
(b) Y is one of the following radicals:

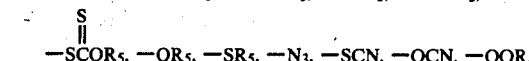

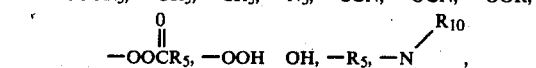

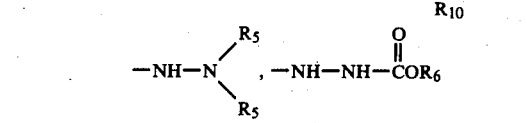

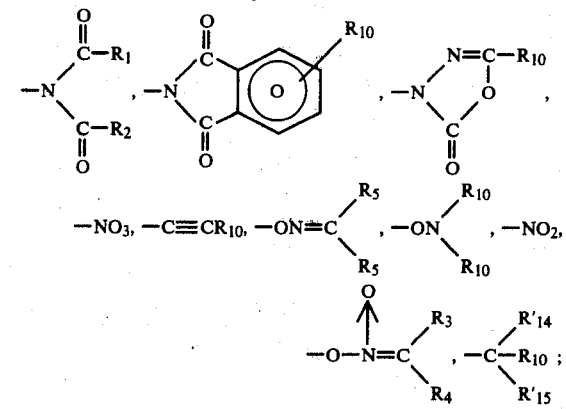

(c) R, $R_1$, $R_2$, $R_3$, $R_4$, $R_5$, $R_6$, $R_{10}$, are as defined hereinbefore;
(d) Y" is one of the following biradicals:

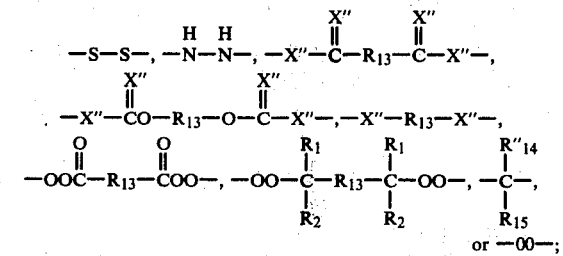

(e) R'$_{14}$ and R'$_{15}$ are

(f) $R_{13}$ is an aliphatic, cycloaliphatic or aromatic biradical and R'$_{14}$ and R'$_{15}$ are as defined hereinbefore; and
(g) X" is oxygen or sulfur.

Compounds prepared by this third process wherein Y is

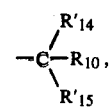

are readily converted to the novel azo compounds wherein Z is

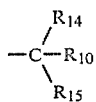

by conventional processes well known to the art.

6. Fourth process: Preparation of amidazo compounds.

Reacting

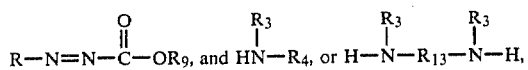

to form the azo products

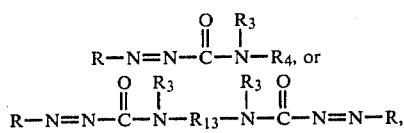

and R$_9$OH where:

(a) R is the radical

with R" being a lower alkyl, aralkyl or phenyl radical and not more than one phenyl is present;

(b) R$_3$ and R$_4$ are hydrogen, lower aliphatic or cycloaliphatic radicals and together may form an alkylene biradical;

(c) R$_9$ is a lower alkyl radical; and (d) R$_{13}$ is an aliphatic, cycloaliphatic or aromatic biradical.

7. Fifth process: Preparation of azoacyl compounds.

(1) Reacting R—NH—NH$_2$ and

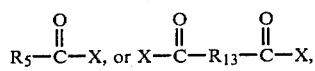

in a liquid solvent which does not contain active hydrogen radicals and in the presence of an alkaline material to form $$(R")_3C—NH—NH—\overset{O}{\overset{\|}{C}}—R_5, \text{ or} \quad (G)$$

$$(R")_3C—NHNH\overset{O}{\overset{\|}{C}}R_{13}\overset{O}{\overset{\|}{C}}NHNHC(R")_3 \quad (G^1)$$

(2) oxidizing G or G$^1$ form the azo products

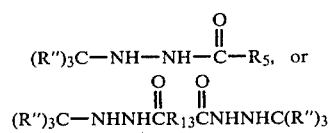

where:

(a) R$_5$ is a lower aliphatic, cycloaliphatic or aromatic radical;

(b) X is a chloro, bromo or iodo radical; and (c) R$_{13}$ is an aliphatic, cycloaliphatic, or aromatic biradical.

8. Sixth process: Preparation of heterosubstituted azo compounds.

(1) Reacting

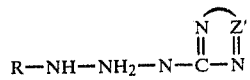

in a liquid solvent which does not contain active hydrogen radicals and in the presence of an alkaline material to form

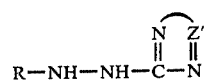 (K)

(2) oxidizing K to form the azo product

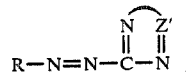 (L)

where:

(a) R is the radical

with R" being a lower alkyl or phenyl radical and not more than one phenyl is present;

(b) Z' is a zero, mono, or divalent remainder of a heterocyclic ring; and (c) X is chloro, bromo or iodo.

9. Seventh process: Preparation of amidohydrazo compounds.

Reacting

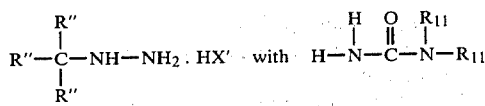

in an aqueous medium at a temperature between about 50° C.–100° C. to form

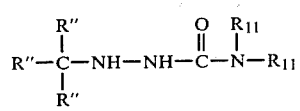

where:

(a) R$_{11}$ is hydrogen or lower alkyl radical; and (b) X' is chloro, bromo, iodo, SO$_4$ or HSO$_4$.

10. Eighth process: Another preparation of amidohydrazo compounds.

Reacting

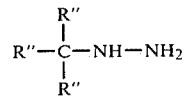

with M'CNO in an aqueous medium to form

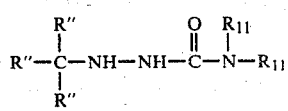

where:
(a) $R_{11}$ is hydrogen or lower alkyl radical; and
(b) M' is a metal or hydrogen radical.

Description of the Inventions

1. Novel Azo Compounds

The scope of the novel azo compounds of the invention has been set out in the summary in connection with Formula I.

The tertiary group joined to one of the azo nitrogens is illustrated by the following

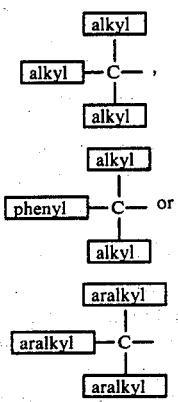

where alkyl indicates a lower alkyl radical, i.e., one having 1 to about 13 carbons and more commonly 1-4 carbon atoms. Tertiary group (a) is preferably a tert-butyl radical. phenyl may include one or more hydrocarbon substitutes such as tolyl and xylyl. aralkyl indicates a group such as benzyl or phenethyl. For convenience the tertiary group is designated $(R'')_3C-$. The compounds having the tri-alkyl-C group are a preferred sub-genus.

The group R' joined to the other azo nitrogen is one of the radicals listed in the difinition of Formula I. These radicals may be designated as t-aliphatic radicals (but not identical to $(R'')_3C-$ in any specific compound), α-substituted tertiary aliphatic radicals, acyl radicals, amido radicals, olefins having the unsaturation adjacent a secondary carbon atom, and nitrogen containing heteroradical, where aliphatic includes cycloaliphatic. The terms aliphatic radical and cycloaliphatic radical are used in their normal chemical meaning—the non-hydrocarbon substituents must not interfere with the preparation reaction(s). In general a lower aliphatic radical will having 1—about 20 carbon atoms and the cycloaliphatic will have 1 or 2 condensed rings and may have hydrocarbon substituents in the ring. Commonly these will be cyclopentyl and cyclohexyl rings.

$R_1$ and $R_2$, $R_3$ and $R_4$, $R_6$ and $R_7$, and $R_7$ and $R_8$ together may form an alkylene biradical. The biradicals may contain 2-30 or more carbon atoms; more commonly 2-16 carbon atoms.

The term aromatic radical is used in its normal chemical sense of a benzene ring or condensed benzene rings which may be substituted by one or more individual groups or a non-aromatic ring. The preferred aromatic radical is a phenyl group.

The group

represents a nitrogen containing heterocyclic radical where [Z'] represents the atoms or groups of atoms which are present in the ring and also the substituents thereon.

The above definitions are broad and intentionally so because the defined R's and Z' appearing in the radical definitions of the azo compounds of Formula I do not affect the general utility of the compounds or the ability to make the compound by the processes set forth herein. Numerous compounds coming with Formula I are set out in the working examples.

Utility

These new compositions are free radical generators, polymerization initiators, curing agents for polyester resins, initiators for free radical initiated chemical reactions, blowing agents for producing foamed polymers and plastics, and selective oxidizing agents.

It has been observed that these new compositions are initiators for the polymerization or copolymerization of unsaturated monomers such as alkenes, vinyl halides, vinyl esters, vinylidene halides and alkenyl aromatics.

Illustrative polymerizable monomers are ethylene, vinyl chloride, vinylidene chloride, vinyl acetate, vinylpyridine, vinylpyrrolidone, vinylcarbazole, butadiene, isoprene, acrylonitrile, acrylic acid, acrylic acid esters, methacrylic acid, methacrylic acid esters, styrene, chlorostyrene and methyl styrenes.

It has also been observed that certain of these novel compounds i.e. Examples I b, and IV b, are especially advantageous initiators in the high pressure polymerization of ethylene.

The new compositions of Formula I, in which R' is one of the defined radicals, excluding —$C(ZR_1R_2)$, also possess very reactive azo linkages. These azo compounds can undergo Diels-Alder reactions, allylic hydrogen additions, and free radical additions at the nitrogen-notrogen double bond as well as thermal decomposition to give free radicals and gas. They are therefore valuable chemical intermediates and reactants.

Specific illustrations of utility are given in the working examples.

Preparation

The new azo compositions of the present invention are easily prepared from hydrazines containing one of the defined tertiary groups R, as shown in the following working examples. The tert-alkylhydrazines have been very difficult and tedious to prepare and have been laboratory curiosities prior to the filing of U.S. patent application Serial No. 409,306, filed 11/5/64 by C. S. Sheppard and L. E. Korczykowski and of common assignment. The new process described in this patent application Ser. No. 409,306 produces tertiary alkylhydrazines in a simple and very economical manner and it is ideally suited for commercial production. Thus, the methods of producing the new compositions of the present invention are economically feasible and are not difficult to carry out on a commercial scale.

Six novel processes for preparation of compounds coming with Formula I are described separately hereinafter.

A process for preparing olefinically substituted unsymmetrical azo compounds is described by B. T. Gillis and J. D. Hagarty, J. Am. Chem. Soc., 87, 4576 (1965), where R is methyl.

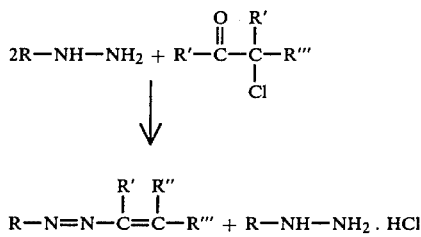

NOVEL PROCESSES FOR AZO COMPOUNDS

First Process

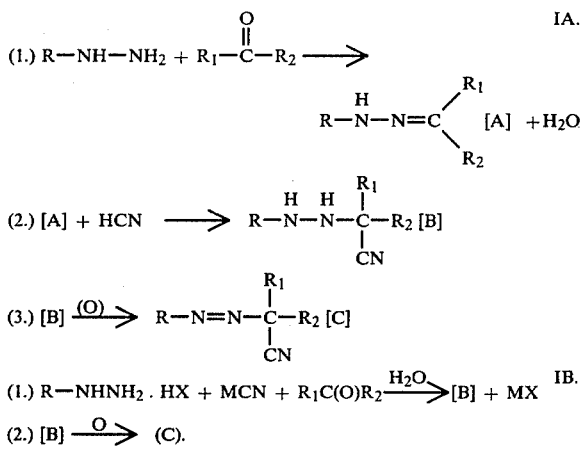

where R is tert-alkyl or tert-aralkyl and $R_1$, $R_2$, and X are as defined above and M is an alkali metal.

When R is a primary and secondary alkyl radical, the [C] compounds are unstable and tautomerize to hydrazones [D]:

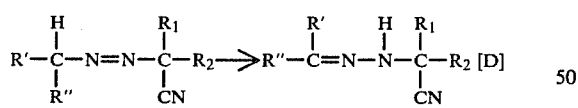

This tautomerization of azo compounds, containing alpha hydrogens, to hydrazones is well known. The rate and extent of the tautomerization is highly dependent upon the nature of the R' and R" radicals and also the pH of the reaction medium. Most primary and secondary alkyl azo compounds tautomerize extremely fast in an acidic medium and the preferred method for oxidizing [B] compounds to the [C] products is with aqueous chlorine, a highly acidic medium. When R is a tertiary alkyl group, no alpha hydrogens are present and therefore no tautomerization occurs. Also, the [C] compounds where R is a primary and secondary alkyl and aralkyl group are not as useful as thermally sensitive free radical and gas generators because the [D] compounds, which would form upon heating [C], are thermally stable. Literature of interest in this area is:

Canadian Patent No. 655,296 issued Jan. 1, 1963.
J. C. Bevington and A. Wahid, Polymer 3, 585 (1962); ibid 4, 129 (1963).
D. Neighbors, et al, J. Am. Chem. Soc. 44, 1561 (1922).
H. Zollinger, "Azo and Diazo Chemistry, Aliphatic and Aromatic Compounds", Interscience, New York, N.Y., 1961, p. 327.

In the first step of this "First IA" process, the defined hydrazine and defined ketone are reacted in the presence of an inert solvent, preferably a benzene or like hydrocarbon, while the water produced is removed substantially continuously during the course of the reaction—in the case of benzene solvent the water goes overhead as a benzene-water azeoptrope. The reaction is carried out at a temperature which will facilitate the preferred distillative removal of water.

In the second step of the "First IA" process, the hydrazone product [A] is reacted with hydrogen cyanide, preferably in the liquid state so as to act as a reaction medium also at a temperature of about 10° to about 80° C., preferably 45°-55° C., to form the cyanohydrazo product [B]. The reaction may also be carried out in the presence of an inert liquid, such as benzene and the like hydrocarbons, ethanol, and water. The reaction time will vary somewhat with the hydrazone and the temperature; 50°-60° C., for example 4-6 hours; at 25° C., as much as 18 hours.

In the final step of the "First IA" process, the hydrazo compound is oxidized under conventional conditions to the corresponding azo compound. For example, the hydrazo compound is contacted with aqueous solution of alkali metal hypohalite or aqueous chlorine at temperatures about the freezing point of water, e.g., 0°-10° C. Optionally, an organic solvent may also be present. Other oxidizing agent include: potassium permanganate, lead tetraacetate, ammonium nitrate, nitric acid, bromine, and the oxides of silver and mercury.

In "step 1" of the first IB process, the water soluble or partially water soluble ketone, the defined hydrazine acid salt and the cyanide are reacted in water at about 10°-80° C. to form the cyanohydrazo product [B].

Other non-limiting details of this First process are to be found in certain working examples herein.

Second Process

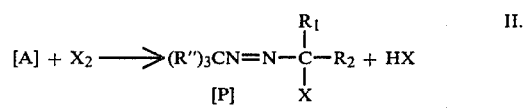

where [A], R, $R_1$, and $R_2$ are as defined above and $X_2$ is bromine or chlorine or iodine.

In this Second Process tert-alkyl- or tertaralkylhydrazones of ketones [A] and chlorine, bromine or iodine are reacted in the presence of an inert solvent, (i.e. a hydrocarbon, a chlorinated hydrocarbon or an aromatic hydrocarbon preferably a petroleum hydrocarbon) at temperatures from −60° C. to +30° C., preferably −10° C. to 15° C., to form the novel [P] compounds.

Other non-limiting details of this Second Process are to be found in certain working examples herein.

-continued

2.) $[P] \xrightarrow{\text{MY'' or}}{\text{H—Y''—H/MOH}}$

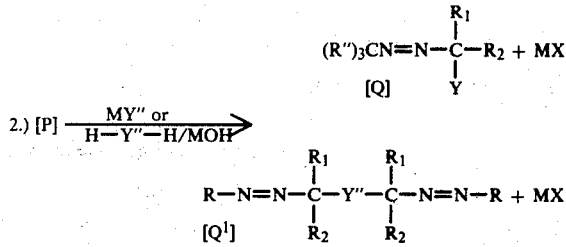

where [P], R, $R_1$, $R_2$, M, Y, and Y" are as defined above. In this Third Process t-alkyl- and aralkylazo-α-halo-alkanes and aralkanes [P] are reacted with the active hydrogen compounds (Y—H or H—Y"—H) in the presence of a base or with the alkali or alkaline earth metal salt of the active hydrogen compound (MY or MY") in solvents, such as pentane, ether, tetrahydrofuran, glyme, alcohols, water, aqueous alcohols and acetone (the solvents, depending on the nature of MY or MY"), at temperature of −10° C. to 60° C., preferably 0° C. to 30° C., to form the novel t-alkyl- and aralkylazo-α-substituted-alkanes and aralkanes [Q] and [$Q^1$].

Prior art relating to the Second and Third Processes is found in the following references:
Goldschmidt and Acksteiner, Ann. 618, 173 (1958)
British Patent No. 988,253 issued Apr. 7, 1961 to Monsanto Co.
Canadian Patent No. 750,380 issued Jan. 10, 1967 to Monsanto Co.

All of these references teach the following reactions:

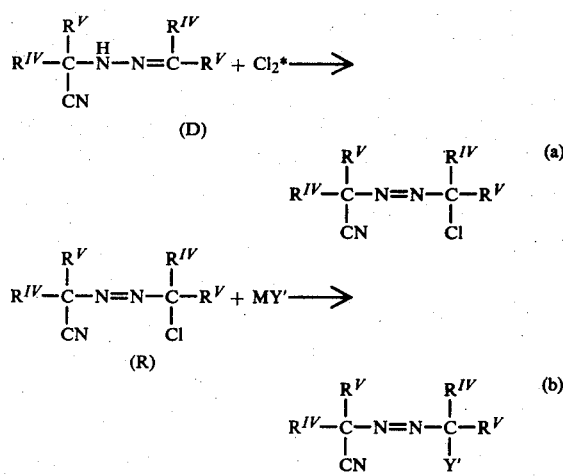

*(Although only chlorine was used, the patents use the word halogen.)

Reaction (a) above is similar to the present Second Process except that the present process uses t-alkyl- and aralkyl- hydrazones (A) whereas reaction (a) above uses cyancalkyl hydrazones (D). The novelty of the present process (Second process) is that it was unknown, prior to the present work, whether a non-cyano t-alkyl- and aralkylhydrazone would react with a halogen to form the novel t-alkyl- and aralkyl-α-haloazo compounds of structure (P).

We have not been able to prepare phenyl-α-haloazocompounds from phenylhydrazones i.e.

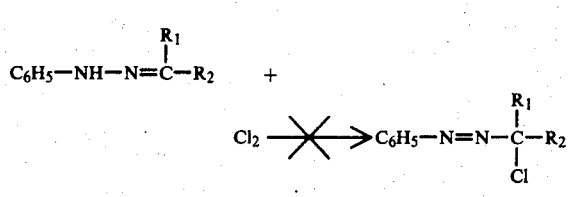

nor have we been able to prepare 3,5,5-trimethyl-3-chloropyrazoline-1 by chlorinating 3,5,5-trimethylpyrazoline-2 (a cyclic t-alkylhydrazone) with chlorine. i.e.

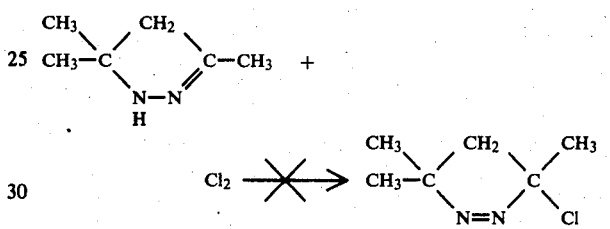

Reaction (b) above is similar to the present Third Process except that the present process uses the novel (P) structures whereas reaction (b) above uses the α-cyanoalkyl-α'-haloalkylazo structures (R). The novelty again is that prior to the present work, it was unknown whether the novel compounds of structure (P) containing no α-cyano group would react with the above defined MY and MY" compounds to form the novel t-alkyl- and aralkyl-α-substituted azo compounds [Q] and [$Q^1$].

We have not been able to react ethoxycarbonyl-α-chloroazo compounds with the MY and MY" compounds under the normal conditions to form the ethoxycarbonyl-α-substituted azo compounds.

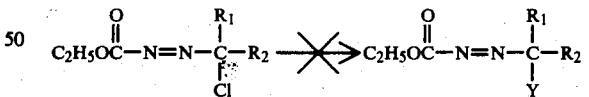

These α-chloro azo compounds were unreactive or decomposed under the above reaction conditions.

Other non-limiting details of the Third Process are to be found in certain working examples.

Fourth Process

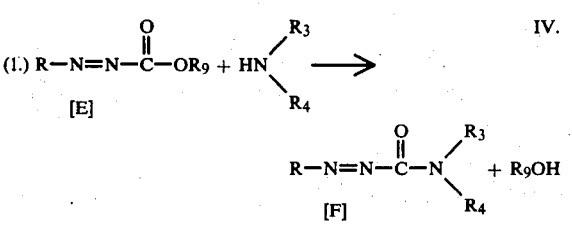

where: $R^{IV}$ and $R^V$ are selected from the class consisting of aliphatic, araliphatic, aromatic, cycloaliphatic and heterocyclic radicals having not more than about 22 carbons and $R^{IV}$ and $R^V$ taken together form cycloalkyl radicals; and Y' is selected from the class consisting of:

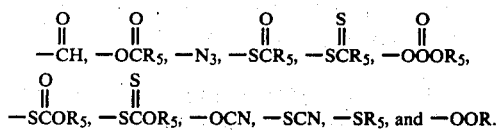

(2.) [E] + 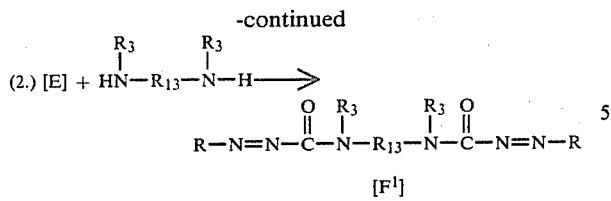 [F¹]

where R, R₃, R₄, and R₁₃ are as defined above and R₉ is a lower alkyl radical. A similar reaction for the case where the azo compound was a diester of azodicarboxylic acid to give azodicarbonamide derivatives is shown in the literature:

H. Bock and J. Kroner, Chem. Ber. 99, 2039 (1966).
K. E. Cooper and E. H. Ingold, J. Chem. Soc. 1926, 1894.

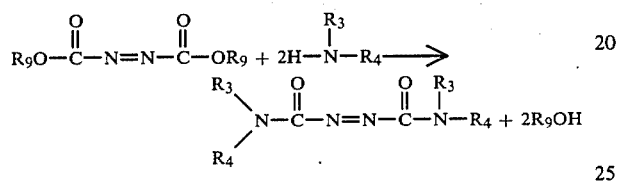

It was unknown, prior to the present work, that a mono azo ester, such as [E], would react with primary and secondary amines (including ammonia) to form the corresponding azoformamide.

The [E] compounds, where R is a tertiary alkyl group, are known. They can be made from t-butylhydrazine and alkyl chloroformates followed by oxidation:

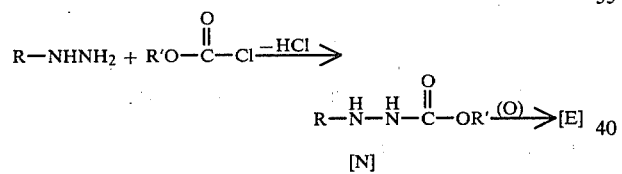
[N]

The [N] compounds can also be prepared directly, without first forming the tertiary alkyl hydrazine, by the process covered in copending patent application Ser. No. 684,652 cited above.

This Fourth Process is preferably carried in a polar solvent such as ethanol, ether and methylene chloride. The reaction temperature is not critical but temperatures on the order of 0°–25° C. are preferred. The working examples herein show that the reaction goes with ammonia, methylamine, dimethyl amine, ethylene diamine, glycine and glycine. Methyl ester, establishing the scope of HNR₃R₄ and HN(R₃)R₁₃N(R₃)H.

Other non-limiting details of the Second Process are to be found in certain working examples.

Fifth Process

V.

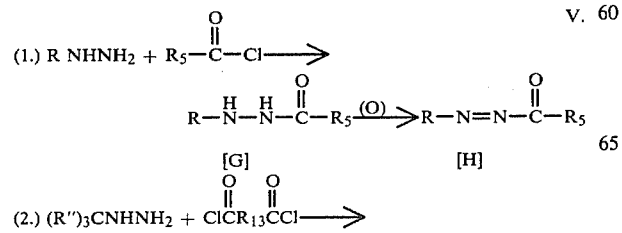

-continued

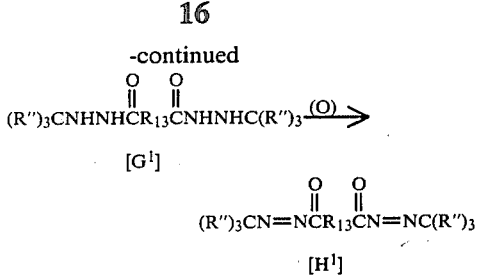

where R, R₅, and R₁₃ are defined as above. This reaction is novel for compounds where R is (R″)₃C- as defined. The reason for this is that when R is a primary and secondary lower alkyl group, [G] is not formed in the first step but instead, [J] is formed as is described by:

J. Lakritz, "The Synthesis and Reactions of Sterically Hindered Hydrazines; And the Acid Catalyzed Rearrangement of Tertiary Cyclic Azides", University of Michigan, Ph.D. thesis, 1960, University Microfilms, Inc., Mio 60-6898.

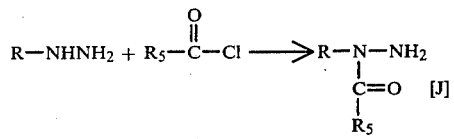

The [J] compounds cannot be oxidized to azo compounds. The formation of [G] rather than [J] when R is a tertiary alkyl group is due to the bulky nature of the tertiary group. This has been previously reported and [G] compounds are known but have never been oxidized to the azo compounds. The azo compounds [H] are very unstable and therefore difficult to isolate.

Symmetrical azo compounds are known, these have been prepared from hydrazine and

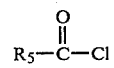

to obtain

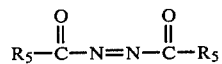

after by oxidation. These azo compounds, however, are significantly different from the [H] compounds of the present invention.

The first step of the Third process may be carried out in water and in organic solvents that do not contain active hydrogens or carbonyl functions and in the presence of a base such as sodium hydroxide, sodium carbonate, tert.-amines, etc.

The second oxidation step of the Third process is carried out as discussed in connection with the First process.

Other non-limiting details of the Third process are to be found in certain working examples.

Sixth Process

VI.

-continued

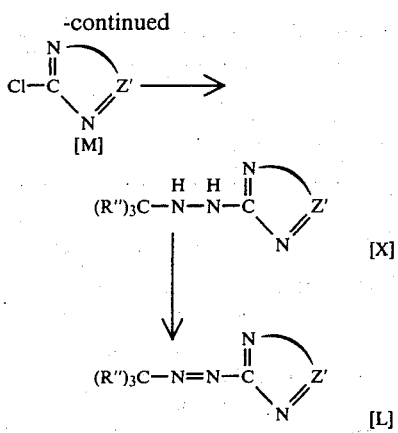

The same chemistry as discussed in the Fifth Process above applies to the cases where "(R")₃" is replaced by a primary and secondary lower alkyl group.

It has been observed that [M] behaves like the acid chlorides and that the operating conditions of the Fifth Process are applicable to this Sixth Process.

2. Novel Hydrazo Compounds

The scope of the hydrazo compounds of the invention has been set in the summary in connection with Formula II.

The discussion with respect to the tertiary group and the radicals R″, R₃ and R₄ in connection with Formula I in the section on azo compounds is entirely applicable to Formula II. Compounds coming within the scope of Formula II are set out in the working examples.

Utility

The 1-(R₃″)C-semicarbazides (II) are useful compounds in the synthesis of compounds of Formula I where R′ is

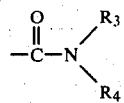

since they can easily be oxidized to I by oxidizing agents such as potassium permanganate, chlorine or bromine.

Specific illustrations of this utility are given in the working examples.

Preparation

Seventh Process

This process consists essentially of heating an aqueous solution of (R″)₃C-hydrazine or its acid salt with a urea, at a temperature of 50° C.–110° C., preferably reflux temperature. For example:

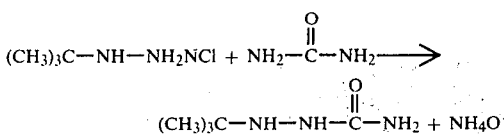

This reaction is broadly stated in the summary at Sixth Process.

Eighth Process

The reaction of a (R″)₃C-hydrazine with a cyanate or cyanic acid in an aqueous system constitutes the Eighth Process. For example:

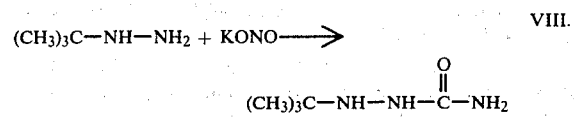

This reaction is broadly stated in the summary at Eighth Process.

Other non-limiting details of these two hydrazo processes are set out in the working examples. 1-Aryl-semicarbazides have been prepared via the Seventh Process but the reaction cannot be generalized for all monosubstituted hydrazines. In the case of the arylhydrazines the unsubstituted nitrogen is the more basic nitrogen due to the electron withdrawing inductive effect of the phenyl group, e.g.

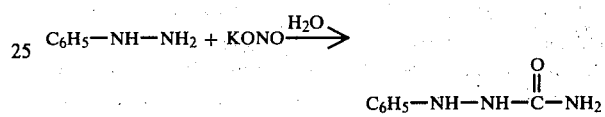

Literature of interest is:
A. Andraca, Anales quim farm 1941, p. 15.
Pellizzari, Gazz. chim. ital. 16, 302 (1888)
Pinner, Ber., 20, 2359
Beilstein, 15, 287

In the case of the monoalkylhydrazines the substituted nitrogen is the more basic nitrogen due to the electron donating effect of the alkyl substituent and reaction generally occurs with the substituted nitrogen in the absence of steric hindrance. In these cases reactions of the Eighth process produce 2-alkylsemicarbazides instead of 1-alkylsemicarbazides, e.g.

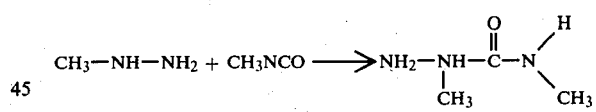

Literature of interest is:
C. Vogelsang, Rec. trav. chim. 62, 5 (1943)
K. A. Taipale and P. V. Usachev, J. Russ. Chem. Soc. 62, 1241–58 (1930)

The 1-alkylsemicarbazides are generally prepared by reduction of the corresponding semicarbazones, a route not applicable for the synthesis of 1-(R″)₃C-semicarbazides as shown by Neighbors et al., supra.

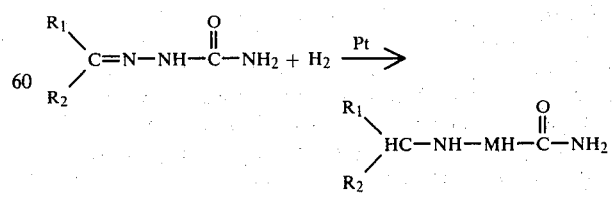

No reference could be found in the literature for the preparation of 1-alkylsemicarbazides by the methods claimed. An attempt was made to prepare 1-methylsemicarbazide by refluxing an aqueous solution of methylhydrazine hydrochloride and urea. No 1-methylsemicarbazide was produced.

EMBODIMENTS OF THE INVENTIONS

Numerous illustrative embodiments of the novel azo compounds, hydrazo compounds and novel processes described hereinbefore and utility thereof are presented in the following 70 working examples. It is to be understood that these examples although numerous are not to be considered as limiting the scope of the inventions as claimed.

EXAMPLE I

Preparation of alpha-(tert.-butylazo)isobutyronitrile

A. Alpha-(tert.-butylhydrazo)isobutyronitrile

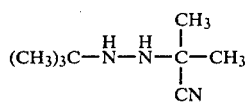

To a stirred solution of 35.2 g. (0.28 m) tert.-butylhydrazine hydrochloride and 13.7 g. (0.28 m) sodium cyanide in 100 ml. of deionized water in a 200 ml. round bottom flask, was added 16.3 g. (0.28 m) acetone. The flask was stoppered and the reaction stirred overnight. The next morning the organic layer was separated, the aqueous layer extracted with 50 ml. methylene chloride and the methylene chloride layer and organic layer combined and dried over anhydrous sodium sulfate. The methylene chloride solution was filtered and the methylene chloride evaporated on a rotating evaporator. The yield was 42.1 g. (96.7%). The infra-red spectrum contained strong NH bands, a cyano band and did not contain any carbonyl or imino bands. Thus the infra-red spectrum was consistent with the structure of the desired product.

B. Alpha-(tert.-butylazo) isobutyronitrile

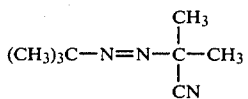

To 8.4 g. (0.054 m) of alpha-(tert.-butylhydrazo) isobutyronitrile in a 4 neck 250 ml. round bottom flask was added with stirring dropwise 100 ml. of a solution containing 0.054 moles of sodium hypochlorite (prepared from 3.85 g. chlorine and 4.5 g. sodium hydroxide in water) holding the temperature below 5° C. with an ice bath. The reaction was stirred an additional twenty minutes after the addition was over and the organic layer separated. The organic layer was washed with 10 ml. of 5% HCl, two 10 ml. portions of saturated NaHCO₃ solution, 10 ml. of deionized water, dried over anhydrous sodium sulfate and the product filtered. The yield was 6.0 g. (72.5%). The infrared spectrum did not contain any N-H bands and was consistent with the structure of the proposed product. The material assayed 99.6% by gas chromatographic analysis. It is a liquid and it is soluble in petroleum solvents.

Alpha-(tert.-butylazo) isobutyronitrile is a thermally sensitive free radical and gas generator. It produces 179 cc. of gas per gram at 110° C. The following half-life data have been determined:

| temp. | t ½ (hrs.) |
|---|---|
| 70° C. | 40.5 |
| 78.8° C. | 10.0 |
| 90° C. | 2.0 |
| 100° C. | 0.54 |
| 110° C. | 0.20 |

EXAMPLE II

Polymerization of Styrene with alpha-(tert.-butylazo) isobutyronitrile

A solution of styrene containing $5 \times 10^{-4}$ moles per deciliter of alpha-(tert.-butylazo)isobutyronitrile was heated at 85° C. and the change in density, which is a measure of polymer formation, was followed by means of a dilatometer to measure polymerization rates at 5% and 10% conversion to polystyrene. The rates obtained at 5% and 10% conversion were $9.73 \times 10^{-3}$ and $9.22 \times 10^{-3}$ moles per liter per minute respectively. Without the alpha(tert.-butylazo)-isobutyronitrile, the 5 and 10% rates were $0.92 \times 10^{-3}$ moles per liter per minute. Thus, this azo compound initiated the polymerization of styrene at 85° C.

EXAMPLE III

Curing an Unsaturated Polyester-Styrene Resin with alpha(tert.-butylazo)isobutyronitrile An unsaturated polyester resin was made by reacting maleic anhydride (1.0 mole), phthalic anhydride (1.0 mole), and propylene glycol (2.2 moles) until an acid number of 45-50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14.

To 20 grams of this blend was added 0.128 gram of alpha-(tert.-butylazo)isobutyronitrile and the resultant composition placed in a constant temperature bath at 212° F. (100° C.). The internal temperature was recorded as function of time and a peak exotherm of 424° F. (217.8° C.) was reached in 4.9 minutes indicating an excellent cure of the unsaturated polyester-styrene resin blend had occurred. At 180° F. (82.2° C.), a peak exotherm of 381° F. (193.9° C.) was obtained in 13.3 minutes. The resultant cured materials were very hard.

Without an initator, no cure of this resin blend occurred after more than 30 minutes at 212° F. (100° C.).

EXAMPLE IV

Preparation of 1-tert.-butylazo-1-cyanocyclohexane

A. 1-tert.-butylhydrazo-1-cyanocyclohexane

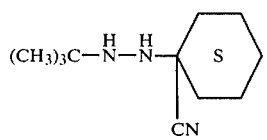

To a rapidly stirred solution of 24.8 g. (0.2 m.) tert.-butylhydrazine hydrochloride and 9.8 g. (0.2 m.) sodium cyanide in 100 ml. of deionized water in a 250 ml. 4 neck round bottom flask, was added a solution of 19.6 g. (0.2 m.) of cyclohexanone in 15 ml. of ethanol. The reaction was stirred for 5 hours at room temperature and then allowed to stand overnight. The next morning the reaction was stirred an additional hour and filtered. The product was dried at 30° C. in a vacuum oven. The yield was 36.3 g. (93.5%) of a white solid melting at 70°-73° C. The white solid evolves HCN on exposure to air over extended periods. The infra-red spectrum contained strong NH bands, a cyano band and did not contain any carbonyl or imino bands. Thus the infra-red spectrum was consistent with the structure of the desired product.

B. 1-tert.-butylazo-1-cyanocyclohexane

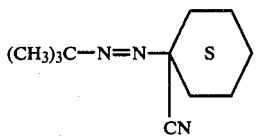

To a rapidly stirred mixture of 39.0 g. (0.2 m.) 1-tert.-butylhydrazo-1-cyanocyclohexane, 200 ml. methylene chloride and 100 ml. water was added 14.3 g. (0.2 m.) chlorine at such a rate that the reaction temperature did not exceed 5° C. The reaction was stirred an additional 15 mins. after the addition was complete. The methylene chloride layer was separated, washed twice with 50 ml. portions of saturated NaHCO$_3$ solution, dried over anhydrous sodium sulfate, filtered and the methylene chloride evaporated on a rotating evaporator to obtain 35.0 g. of liquid product that assayed 86.5% by an ultra violet spectrophotometric analysis. Distillation gave a product, b.p. 71° C./1.2 mm. of Hg that assayed 97.6% as 1-tert.-butylazo-1-cyanocyclohexane. The infrared spectrum was in accord with this structure.

1-tert.-butylazo-1-cyanocyclohexane is a thermally sensitive free radical and gas generator. It produces 146 cc. of gas per gram at 130° C. The following half-life data have been determined:

| temp. | t ½ (hours) |
|---|---|
| 96.3° C. | 10.0 |
| 100° C. | 6.7 |
| 110° C. | 2.3 |
| 120° C. | .75 |

EXAMPLE V

Polymerization of Styrene with 1-tert.-butylazo-1-cyanocyclohexane

The procedure of Example II was used at 85° C. and 100° C. The rates obtained at 5% and 10% conversion at 85° C. were 3.68×10$^{-3}$ and 3.33×10$^{-3}$ moles per liter per minute respectively and at 100° C. they were 13.3×10$^{-3}$ moles per liter per minute. Without the 1-tert.-butylazo-1-cyanocyclohexane, the 5% and 10% rates at 100° C. were 2.81×10$^{-3}$ moles per liter per minute.

EXAMPLE VI

Curing an Unsaturated Polyester-styrene Resin with 1-tert.-butylazo-1-cyanocyclohexane The procedure of Example III was used at 212° F. (100° C.) and 240° F. (115.6° C.) where peak exotherms of 414° F. (212.2° C.) and 440° F. (226.7° C.) were obtained after 10.0 and 5.3 minutes respectively using 0.2 gram of the 1-tert.-butylazo-1-cyanocyclohexane. The resultant cured resins were very hard.

EXAMPLE VII

Preparation of 4-tert.-butylazo-4-cyano-2,6-dimethylheptane

A. tert.-butylhydrazone of diisobutylketone

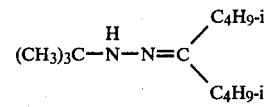

The tert.-butylhydrazone of diisobutylketone was prepared in 94.5% yield by heating a solution of 5.0 g. (0.057 m) tert.-butylhydrazine, 8.1 g. (0.057/m.) diisobutylketone and 0.1 g. p-toluene-sulfonic acid in benzene and azeotroping off the water formed in the reaction. The reaction was refluxed four hours and the benzene evaporated off on a rotating evaporator. The liquid product weighed 11.45 g. (94.5%) and the infrared spectrum was consistent with the proposed structure.

B. 4-tert.-butylhydrazo-4-cyano-2,6-dimethylheptane

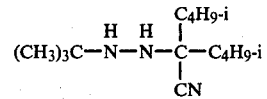

4-tert.-butylhydrazo-4-cyano-2,6-dimethylheptane was prepared in 99% yield by heating a solution of 11.0 g. of diisobutylketone tert.-butylhdrazone in 20 ml. of liquid HCN at 50° C. for 6 hours. The excess HCN was evaporated off into a dry ice trap leaving 12.1 g. (99% of the liquid product. The infra-red spectrum was consistent with the proposed structure of the compound (strong NH and weak CN bands).

C. 4-tert.-butylazo-4-cyano-2,6-dimethylheptane

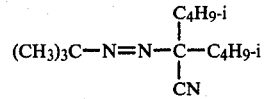

To a rapidly stirred mixture of 12.1 g. (0.046 m.) of 4-tert.-butylhydrazo-4cyano-2,6-dimethylheptane, 30 ml. methylene chloride and 15 ml. water was added 7.35 g. (0.046 m.) bromine at such a rate that the reaction temperature did not exceed 5° C. The reaction was stirred an additional 15 minutes after the addition was complete. The methylene chloride layer was separated, washed twice with 50 ml. portions of saturated NaHCO$_3$ solution, dried over anhydrous sodium sulfate, filtered, and the methylene chloride evaporated on a rotating evaporator to obtain 11.5 grams of liquid product. The infra-red spectrum was in accord with the structure of 4-tert.-butylazo-4-cyano-2,6-dimethylheptane.

4-tert.-butylazo-4-cyano-2,6-dimethylheptane is a thermally sensitive free radical and gas generator that begins to evolve nitrogen slowly at 70° C. At a 1.0 weight percent loading it cured the unsaturated polyester-styrene resin of Example III at 180° F. (82.2° C.) giving a peak exotherm of 371° F. in 2.8 minutes and a very hard cured resin.

EXAMPLE VIII

Preparation of 1-tert.-butylazo-1-cyano-3,3,5-trimethylcyclohexane

A. tert.-butylhydrazone of dihydroisophorone

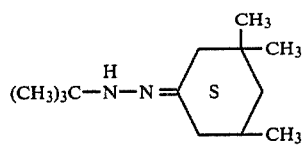

The same procedure as was used in Example VII A was used for the preparation of dihydroisophorone tert.-butylhydrazone. The yield of liquid product was 12.0 g. (100%) and the infra-red spectrum was consistent with the structure of the proposed compound.

B. 1-tert.-butylhydrazo-1-cyano-3,3,5-trimethylcyclohexane

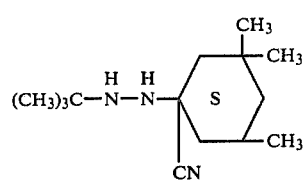

1-tert.-butylhydrazo-3,3,5-trimethylcyclohexane was prepared in the same manner as 4-tert.-butylhydrazo-4-cyano-2,6-dimethyhlheptane in Example VII B. The liquid product was used in the next step directly.

C. 1-tert.-butylazo-1-cyano-3,3,5-trimethylcyclohexane

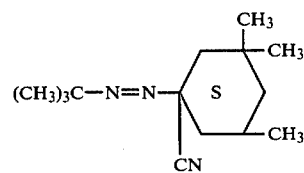

1-tert.-butylazo-1-cyano-3,3,5-trimethylcyclohexane was prepared by bromine oxidation of the above 1-tert.-butylhydrazo-1-cyano-3,3,5-trimethylcyclohexane in the same way that 4-tert.-butylhydrazo-4-cyano-2,6-dimethylheptane was oxidized in Example VII C. The yield of liquid product was 8.2 g. (63%) and the infrared spectrum was consistent with the structure of the proposed compound.

1-tert.-butylazo-1-cyano-3,3,5-trimethylcyclohexane is a thermally sensitive free radical and gas generator which begins to evolve nitrogen slowly at 100° C. At a 1.0 weight percent loading it oured the unsaturated polyester-styrene resin of Example III at 180° F. (82.2° C.) giving a peak exotherm of 384° F. (195.6° C.) in 9.4 minutes and a very hard cured resin.

EXAMPLE IX

Preparation of 2-tert.-butylazo-2-cyano-3,3-dimethylbutane

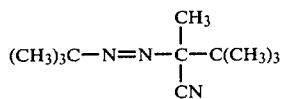

A. Pinacolone tert.-butylhydrazone

To a solution of 5 g. (0.05 m.) pinacolone in 50 ml. benzene was added 5 g. (0.057 m.) tert.-butylhydrazine and a spatula tip of para-toluenesulfonic acid. The flask was fitted with a Dean Stark trap and the reaction refluxed until 0.9 ml. (0.05 m.) of water was azeotroped off. The solution was cooled down and the benzene stripped off leaving 8.5 g. (100%) of a white fluffy solid. The infra-red spectrum of the solid was consistent with the structure of the proposed compound.

B. 2-tert.-butylhydrazo-2-cyano-3,3-dimethylbutane

To a solution of 7.0 g. (0.0413 m.) of pinacolone tert.-butylhydrazone in 20 ml. of benzene in a pressure bottle was added 20 ml. of liquid HCN. The bottle was stoppered and the reaction heated at 50° C. for 4 hours. The reaction cooled down and the benzene and HCN stripped off. The yield was 8.0 g. of a crude solid. The solid was dissolved in pentane, the pentane solution dried over anhydrous sodium sulfate, filtered, and the pentane stripped off. The yield was 7.7 g. (94%) of a tan solid, melting range 67°–74° C. The infra-red spectrum was consistent with the structure of the proposed product.

C. 2-tert.-butylazo-2-cyano-3,3-dimethylbutane

To a mixture of 7.7 g. (0.039 m.) 2-tert.-butylhydrazo-2-cyano-3,3-dimethylbutane, 50 ml. methylene chloride and 25 ml. water, cooled to 0° in an ice bath, was added 6.25 g. (0.039 m.) bromine dropwise over 15 minutes holding the temperature at 0° to 5° C. After the bromine addition, the reaction was stirred 10 minutes, the methylene chloride layer separated, washed twice with 10% NaHCO₃ solution, dried over anhydrous sodium sulfate, filtered and the methylene chloride evaporated off. The yield was 7.6 g. (100%) of a white solid with a melting range of 38°–40° C. Its infra-red curve was in accord with the structure of 2-tert.-butylzao-2-cyano-3,3-dimethylbutane. The product is a thermally sensitive free radical and gas generating compound that begins to evolve nitrogen at 95° C.

It cured the unsaturated polyester-styrene resin of Example III at 180° F. (82.2° C.) and 212° F. (100° C.) giving peak exotherms of 388° F. (197.8° C.) and 430° F. (221.1° C.) in 10.4 and 4.9 minutes respectively. The cured samples were very hard.

EXAMPLE X

Preparation of alpha-tert.-butylazo-alpha-methyl-gamma-carboxybutyronitrile

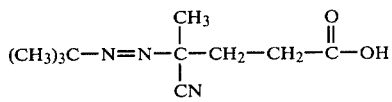

To a mixture of 5.1 g. (0.0438 m.) levulinic acid in 25 ml. water was added in the following sequence: 3.52 g. (0.0438 m.) 50% sodium hydroxide, 2.94 g. (0.06 m.) sodium cyanide and 5.45 g. (0.0438 m.) tert.-butylhydrazine hydrochloride. The reaction mixture was stirred for 5 hours at room temperature, cooled to 5° C. and chlorine passed into the system holding the temperature below 15° C. until there was an increase in weight of 5.0 g. (0.07 m.). After the chlorination was over, the product was extracted with methylene chloride, the methylene chloride solution washed twice with water, dried over anhydrous sodium sulfate, filtered, and the methylene chloride evaporated off on a rotating evaporator. The crude yield was 4.85 g. (52.5%). The crude material was recrystallized from benzene-pentane to give 4.0 g. of product having a melting range of 79°–81° C. The infra-red spectrum was consistent with the structure of the proposed compound.

Alpha-tert.-butylazo-alpha-methyl-gamma-carboxybutyronitrile is a thermally sensitive free radical and gas generating compound which begins to evolve nitrogen at 85° C. The half-life of this compound is 55½ hours at 65° C., 11.0 hours at 75° C. and 3.15 hours at 85° C.

It cured the unsaturated polyester-styrene resin of Example III at 180° F. (82.2° C.) and 212° F. (100° C.) at a 1.0 weight percent loading giving peak exotherms of 410° F. (210.0° C.) and 422° F. (216.7° C.) in 8.5 and 3.8 minutes respectively. The cured samples were very hard.

EXAMPLE XI

Preparation of alpha-(tert.-cumylazo)isobutyronitrile

A. Alpha-(tert.-cumylhydrazo)isobutyronitrile

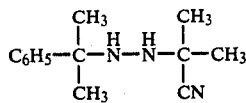

The tert.-cumylhydrazone of acetone (19.0 g.) was treated with an aqueous solution of excess hydrocyanic acid at R.T. This mixture was stirred for 6 hours and then allowed to stand overnight. The reaction mixture was then extracted with methylene chloride. The methylene chloride extracts were dried over anhydrous sodium sulfate, filtered and the methylene chloride evaporated to obtain a product (21.5 g.) that had an infra-red spectrum in accord with the structure of alpha-(tert.-cumylhydrazo)isobutyronitrile. The product was used without further purification in the next step.

B. Alpha-(tert.-cumylazo)isobutyronitrile

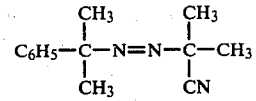

The crude hydrazo product from above (21.4 g.) was dissolved in 100 ml. methylene chloride, 50 ml. of water added and the mixture cooled to 0° C. Chlorine was passed into the solution at 0.4 g./min. until 7.1 g. of chlorine had been added. The temperature was held at 0°–3° C. throughout the addition. At the end of the addition the methylene chloride layer was separated, washed twice with saturated, NaHCO₃, dried over anhydrous sodium sulfate, filtered and the methylene chloride evaporated leaving 18.6 g. of crude alpha-(tert-cumylazo)isobutyronitrile. A sample of the crude alpha-(tert-cumylazo)isobutyronitrile (8.75 g.) was chromatographed through aluminia and 6.0 g. of the pure liquid alpha-(tert-cumylazo)isobutyronitrile was obtained as evidenced by infra-red spectroscopy.

Alpha-(tert-cumylazo)isobutyronitrile is a thermally sensitive free radical and gas generator which begins to evolve nitrogen slowly at 55° C.

At a 1.0 weight percent loading, it cured the unsaturated polyester-styrene resin of Example III at 180° F. (82.2° C.) giving a peak exotherm of 378° F. (192.2° C.) in 1.3 minutes and a very hard cured resin.

EXAMPLE XII

Preparation of alpha-tert-butylazo-alpha-cyclopropylpropionitrile

A. Tert.butylhydrazone of methyl cyclopropyl ketone

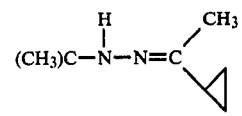

The same procedure as was used in Example VII A was used for the preparation of methyl cyclopropyl ketone tert-butylhydrazone. The yield of liquid product was 8.8 g. (100%) and the infra-red spectrum was consistent with the structure of the proposed compound.

B. Alpha-tert-butylhydrazo-alpha-cyclopropylpropionitrile

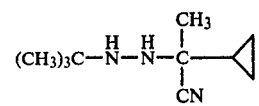

A solution of 8.7 g. methyl cyclopropyl ketone tert-butyl-hydrazone in 20 ml. liquid hydrocyanic acid was heated for 6 hours in a pressure bottle at 60° C. The solution was cooled, poured into ice water and the aqueous solution extracted twice with ether. The ether extracts were combined, washed with saturated sodium bicarbonate solution dried over sodium sulfate, filtered and the ether evaporated off. The yield was 10.0 g. (99%) of a brown liquid. The infra-red spectrum was consistent with the structure of the proposed product.

C. Alpha-tert-butylazo-alpha-cyclopropylpropionitrile

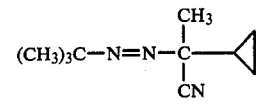

To a mixture of 10.0 g. (0.055 m.) of crude alpha-tert-butylhydrazo-alpha-cyclopropionitrile, 100 ml. methylene chloride, and 50 ml. water, cooled to 0° C. in an ice bath, was added 8.75 g. (0.055 m.) of bromine dropwise over 15 minutes holding the temperature at 0° to 5° C. After the bromine addition, the reaction was stirred 10 minutes, the methylene chloride layer separated, washed twice with saturated sodium bicarbonate solution, dried over anhydrous sodium sulfate, filtered and the methylene chloride evaporated off. The yield was 8.9 g. (90%) of a brown liquid. The liquid was chromatographed over an alumina column, eluting it with pentane, to give 8.1 g. of a light tan liquid which solidifies in the freezer. The infra-red spectrum was consistent with the structure of the proposed compound. The product is a thermally sensitive free radical and gas generating compound that begins to evolve nitrogen at 75° C.

Alpha-tert.-butylazo-alpha-cyclopropyl propionitrile cured the unsaturated polyester-styrene resin of Example III at 180° F. (82.2° C.) and 212° F. (100° C.) giving peak exotherms of 403° F. (206.1° C.) and 420° F. (215.6° C.) in 3.3 and 2.1 minutes respectively. The cured samples were very hard.

EXAMPLE XIII

Preparation of tert.-butylazoformamide

Ammonia gas was slowly bubbled into a solution of 5.4 g. (0.0314 m.) of isopropyl tert.-butylazocarboxylate in 25 ml. of 95% ethanol holding the temperature at 10° C.±5° with an ice bath. The ammonia addition was continued 5 minutes after the exotherm subsided. The reaction was stirred an additional hour at room temperature and the alcohol evaporated off on the rotating evaporator. The crude residue was slurried in 10 ml. pentane and the crystals filtered off. The yield was 3.4 g. (84%) of a yellow solid (m.p. 103°–105° C.) that assayed 98.3% by an iodometric titration. The infra-red spectrum is consistent with the structure of tert.-butylazoformamide.

Tert.-butylazoformamide is a thermally sensitive free radical and gas generator. The following half-life data have been determined by gas evolution technique using trichlorobenzene as the solvent:

| temp. ° C. | t ½ (hours) |
| --- | --- |
| 150° | 0.14 |
| 130° | 0.87 |
| 120° | 3.00 |
| 110° | 5.73 |

It cured the unsaturated-polyester-styrene resin of Example III at a 1.0 weight percent loading at temperature of 212° F. (100° C.), 240° F. (115.6° C.), and 265° F. (129.4° C.) giving peak exotherms of 407° F. (208.0° C.), 430° F. (221.1° C.), and 438° F. (225.6° C.) in 7.1, 5.9, and 4.5 minutes respectively. The cured samples were very hard.

EXAMPLE XIV

Preparation of tert.-butylazo-N-methylformamide

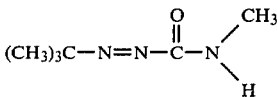

Methylamine was slowly bubbled into a solution of 5.0 g. (0.0346 m.) methyl tert.-butylazocarboxylate in 25 ml. of 95% ethanol holding the temperature at 10° C.±5° C. with an ice bath. The methylamine addition was continued 5 minutes after the exotherm subsided. The reaction was stirred an additional ½ hour at room temperature and the ethanol and excess methylamine were evaporated off on the rotating evaporator. The yield was 5.0 g. (100%) of crude material or 4.6 g. (92%) after washing with pentane. The purified product had a melting range of 34°–36° C. and assayed 97.7% by an iodometric analysis. The infra-red spectrum was consistent with the structure of tert.-butylazo-N-methylformamide.

It cured the unsaturated polyester-styrene resin of Example III at a 1.0 weight percent loading at 265° F. (129.4° C.) giving a peak exotherm of 428° F. (220.0° C.) in 17.1 minutes and a very hard cured resin.

EXAMPLE XV

Preparation of tert.-butylazo-N,N-dimethylformamide

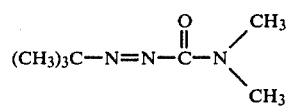

Dimethylamine was slowly bubbled into a solution of 5.0 g. (0.0346 m.) methyl tert.-butylazocarboxylate in 25 ml. of 95% ethanol holding the temperature at 10° C.±5° with an ice bath. The dimethylamine addition was continued 5 minutes after the exotherm subsided. The reaction was stirred an additional ½ hour at room temperature and the ethanol and excess dimethylamine were evaporated off on the rotating evaporator. The yield was 5.45 g. (100%) of a yellow liquid which crystallized in the freezer. The material assayed 92.1% by an iodometric analysis and the infra-red spectrum was consistent with the structure of tert.-butylazo-N,N-dimethylformamide.

The product is useful oxidizing agent as evidenced by the fact that it oxidized iodide ion to free iodine.

EXAMPLE XVI

Preparation of tert.-butylazo-N-carbmethoxymethylformamide

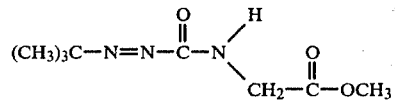

To a solution of 3.4 g. (0.27 m.) of the hydrochloride of glycine methyl ester in 20 ml. water was added 2.16 g. (0.027 m.) 50% sodium hydroxide. The solution was cooled to 5° C. and a slow addition of 3.75 g. (0.026 m.) methyl tert.-butylazocarboxylate in 15 m. ethanol begun. The addition required 15 minutes and the reaction was stirred an additional 2 hours after the addition was over. The homogeneous solution was then poured into 50 ml. water and the aqueous solution extracted three times with methylene chloride. The methylene chloride layers were combined, dried over anhydrous sodium sulfate, filtered and the methylene chloride evaporated off. The yield was 4.35 g. (83%) of a yellow solid. The crude product was recrystallized from benzene-pentane. The recrystallized material had a melting range of 88°–90° C. and assayed 99.0% by an iodometric titration.

The infra-red spectrum is consistent with the structure of tert.-butylazo-N-carbmethoxymethylformamide. The product is a thermally sensitive free radical and gas generating compound that begun to evolve nitrogen at 140° C. It is also an oxidizing agent that oxidized iodide ion to free iodine.

It cured the unsaturated polyester-styrene resin of Example III at a 1.0 weight percent loading at 240° F. (115.6° C.) and 265° F. (129.4° C.) giving peak exotherms of 356° F. (180.0° C.) and 484° F. (251.1° C.) in 15.8 and 5.1 minutes respectively. The cured samples were very hard.

EXAMPLE XVII

Preparation of tert.-butylazo-N-carboxymethylformamide

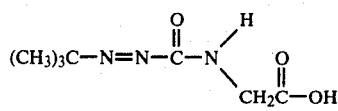

To a solution of 3.0 g. (0.04 m.) glycine in 30 ml. water was added 3.2 g. (0.04 m.) 50% sodium hydroxide. The solution was cooled to 5° C. and a slow addition of 5.0 g. (0.0337 m.) methyl tert.-butylazocarboxylate in 10 ml. ethanol begun. The addition required 15 minutes and the reaction was stirred an additional 2 hours at room temperature. A few drops of 50% sodium hydroxide were added and the solution extracted with methylene chloride to remove any unreacted methyl tert.-butylazocarboxylate. The methylene chloride layer was colorless and was discarded. The aqueous layer was made acidic (pH=2) by adding concentrated hydrochloric acid and extracted with 4–50 ml. portions of methylene chloride. The methylene chloride layers were combined, dried over anhydrous sodium sulfate, filtered and the methylene chloride evaporated off. The yield was 5.5 g. (86.5%) of a yellow viscous liquid which crystallized on standing in the freezer. The crude product assayed 77.4% by an iodometric analysis and the infra-red spectrum was consistent with the structure of tert.-butylazo-N-carboxymethylformamide. The product is a thermally sensitive compound that begins to evolve nitrogen at 60° C. It is also an oxidizing agent that oxidized iodide ion to free iodine.

EXAMPLE XVIII

Preparation of tert.-cumylazoformamide

A. 1-tert.-cumyl-2-carbisopropoxyhydrazine

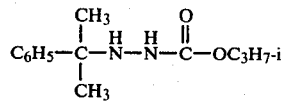

A solution of 12.3 g. (0.051 m.) of the oxalic acid salt of tert.-cumylhydrazine was slurried in 100 ml. water and the solution made basic by adding 17.0 g. (0.212 m.) of 50% sodium hydroxide. The resulting sodium oxalate was filtered off, washed with 25 ml. water and the filtrate transferred to a reactor.

To the rapidly stirred solution was added 6.25 g. (0.0512 m.) isopropyl chloroformate and the reaction stirred at room temperature for an additional 3 hours. Methylene chloride (100 ml.) was added and the reaction stirred an additional hour, the methylene chloride layer separated and the aqueous phase extracted twice with 100 ml. methylene chloride. The methylene chloride layers were combined, dried over anhydrous sodium sulfate, filtered and the methylene chloride evaporated off on a rotating evaporator. The yield was 10.8 g. (89.5%) of a viscous liquid. The infra-red spectrum was consistent with the structure of the proposed compound.

B. Isopropyl tert.-cumylazocarboxylate

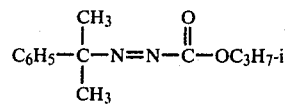

To a solution of 10.8 g. (0.0458) of crude 1-tert.-cumyl-2-carbisopropoxyhydrazine in 100 ml. methylene chloride was added 50 ml. water and the mixture cooled to 5° C. Bromine, 8.0 g. (0.050 m.), was added dropwise to this stirred mixture holding the temperature at 5°–10° C. with an ice bath. The reaction was stirred an additional 15 minutes at 5° C. The methylene chloride layer separated, washed twice with NaHCO₃ solution, dried over anhydrous sodium sulfate and the methylene chloride evaporated off on a rotating evaporator. The product was placed in the freezer for an hour and a small amount of white solid crystallized out. The product was filtered, the solid washed with pentane, and the pentane evaporated from the filtrate. The yield was 9.8 g. (91.5%) of a yellow liquid. The infra-red spectrum of the product was in agreement with the structure of the proposed compound. The product assayed 88.5% by an iodometric titration.

Isopropyl tert.-cumylazocarboxylate is a thermally sensitive compound and slowly evolves nitrogen at 80° C.

C. Tert.-cumylazoformamide

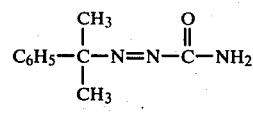

To a solution of 4.9 g. (0.0185 m.) of 88.5% isopropyl tert.-cumylazocarboxylate in 25 ml. ethanol, cooled to 5° C. in an ice bath, was passed a slow stream of ammonia. There was a slight exotherm and the temperature slowly rose to 15° C. When the temperature began to drop the ammonia addition was stopped. The reaction was stirred an additional 15 minutes and the yellow solid which formed was filtered off. The filtrate was evaporated to dryness and the resulting yellow solid washed with pentane to remove any unreacted isopropyl cumylazocarboxylate. The two crops were combined and the yield was 3.2 g. (90.5%). The yellow solid was recrystallized from benzene. The melting range of the recrystallized material was 140°–143° C. and it assayed 100% by an iodometric titration.

Tert.-cumylazoformamide is a thermally sensitive free radical and gas generating compound. It rapidly evolves nitrogen upon melting. It oxidized iodide ion to free iodine. It cured the unsaturated polyester-styrene resin of Example III at a 1.0 weight percent loading at 240° F. (115.6° C.) and 265° F. (129.4° C.) giving peak exotherms of 422° F. (216.7° C.) and 454° F. (234.4° C.) in 10.3 and 6.0 minutes respectively. The cured samples were very hard.

EXAMPLE XIX

Preparation of Pivaloyl tert-butyldiimide

A. 1-Pivaloyl-2-tert.-butylhydrazine

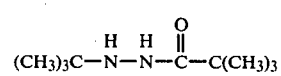

A solution of 40.8 g. (0.33 m.) of tert.-butylhydrazine hydrochloride in 300 ml. of distilled water was placed in a 500 ml. 4 neck, round bottom flask equipped with a high speed mechanical stirrer, a thermometer and a condenser, and cooled to 10° C. The solution was made basic by adding 24.3 g. (0.225 m.) of sodium carbonate and then 18.9 g. (0.15 m.) of pivaloyl chloride was added dropwise over 1 hour holding the temperature below 10° C. with an ice bath. The mixture was stirred for 3 hours and the white solid which formed was filtered off and dried. The product weight 16.5 g. after drying and had a melting range of 97°–105° C.

The aqueous filtrate was extracted with methylene chloride, the methylene chloride solution dried and the methylene chloride evaporated off on a rotating evaporator. The resultant solid weighed 5.9 g. and had a melting range of 98°–101° C. The infra-red spectra of the two solids were identical and were also consistent with the structure of 1-pivaloyl 2-tert.-butylhydrazine. The total yield was 22.4 g. (86.5%).

B. Pivaloyl tert.-butyldiimide

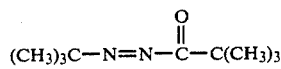

To a solution of 5.9 g. (0.0343 m.) of 1-pivaloyl-2-tert.-butylhydrazine in 100 ml. of methylene chloride cooled to 5° C., was added 75 ml. of a sodium hypochlorite solution as fast as possible without exceeding a reaction temperature of 5° C. The sodium hypochlorite solution was prepared by adding 2.4 g. (0.0343 m.) chlorine to 75 ml. of a solution containing 2.7 g. of (0.0686 m.) of sodium hydroxide. The reaction was stirred an additional 10 minutes at 5° C. after the addition of the sodium hypochlorite solution. The methylene chloride layer was separated. The methylene chloride solution was washed once with sodium bicarbonate solution, dried over anhydrous sodium sulfate, filtered, and the methylene chloride evaporated off on the rotating evaporator. An orange liquid with a solid suspended in it was obtained. Pentane (20 ml.) was added to the solution and the solution cooled in the freezer. The pentane solution was filtered and the filtrate evaporated to dryness leaving 2.0 g. (36%) of the liquid pivaloyl tert.-butyldiimide. The product assayed 77.7% by an iodometric titration and its infra-red spectrum was consistent with the proposed structure.

The white solid was not identified; it is thought to be a decomposition product.

Pivaloyl tert.-butyldiimide is a thermally unstable compound and evolves nitrogen at 35° C. It cured the unsaturated polyester-styrene resin of Example III at a 1.0 weight percent loading at room temperature and at 180° F. (82.2° C.) giving peak exotherms of 139° F. (59.4° C.) and 289° F. (142.8° C.) in 34.1 and 4.9 minutes respectively. The 180° F. (82.2° C.) cured sample was very hard.

EXAMPLE XX

Preparation of Benzoyl tert.-butyldiimide

A. 1-Benzoyl-2-tert.-butylhydrazine

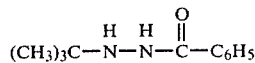

1-benzoyl-2-tert.-butylhydrazine was prepared in 71% yield by adding benzoyl chloride to a basic solution of t-butylhydrazine in water. The procedure was the same as that for preparing 1-pivaloyl-2-tert.-butylhydrazine in Example XIX A. The product has a melting range of 94°–95° C. and its infra-red spectrum was consistent with that of the proposed structure.

B. Benzoyl tert.-butyldiimide

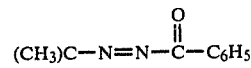

Benzoyl tert.-butyldiimide was prepared by the oxidation of 1-benzoyl-2-tert.-butylhydrazine with sodium hypochlorite in the same manner as the preparation of pivaloyl tert.-butyldiimide in Example XIII B. The yield was 40% of red liquid benzoyl tert.-butyldiimide which assayed 71.7% by an iodometric analysis and its infra-red spectrum was consistent with the proposed structure.

The solid impurities present in the crude azo were not identified but they are thought to be decomposition products since their infra-red spectrum was different from the starting hydrazo compound.

Benzoyl tert.-butyldiimide is a thermally unstable compound and evolves nitrogen at 25° C. It cured the unsaturated polyester-styrene resin of Example III at a 1.0 weight percent loading at 180° F. (82.2° C.) giving a peak exotherm of 233° F. (112.0° C.) in 10.0 minutes and a hard cured resin.

EXAMPLE XXI

Preparation of 2,4,6-tri-(tert.-butylazo)-1,3,5-triazine

A. 2,4,6-Tri-(tert.-butylhydrazo)-1,3,5-triazine

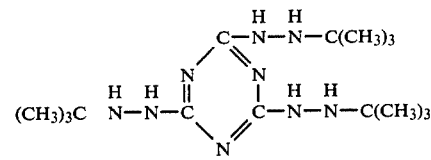

To a solution of 5.55 g. (0.06 mole) of 95% tert.-butylhydrazine in 25 ml. of anhydrous ether at 5° to 10° C. was added, with stirring, a solution of 1.85 g. (0.01 mole) of cyanuric chloride in 35 ml. of anhydrous ether from a dropping funnel. The addition rate was such that the temperature was maintained at around 10° C. The stirred reaction mixture was then slowly warmed to room temperature where it was allowed to stand overnight. The mixture was then filtered. The solid filter cake was triturated with water and the resultant water washed white solid dried to obtain 0.62 g. (18.3% yield) of product, m.p. 189°–190° C., having an infra-red spectrum that was in accord with the structure of 2,4,6-tri-(tert.-butylhydrazo)-1,3,5-triazine.

B. 2,4,6-Tri-(tert.-butylazo)-1,3,5-triazine

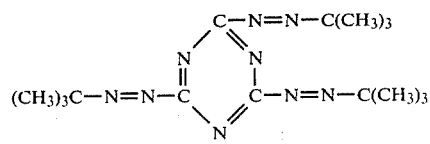

0.55 g. of the above 2,4,6-tri-(tert.-butylhydrazo)-1,3,5-triazine was dissolved in 50 ml. of water to which 1 ml. of concentrated hydrochloric acid was added. The resultant solution was cooled to below 5° C. and then 0.115 g. of chlorine gas was admitted over a 2½ minute period. The reaction mixture was stirred at 5° C. for another 15 minutes and then allowed to stand at 5° C. for one hour. Then 75 ml. of ether were added. The reaction mixture was stirred and then the ether layer separated. The water layer was washed with ether and the combined ether layers washed with saturated aqueous sodium chloride until the water extracts were neutral. The ether solution was dried over anhydrous sodium sulfate, filtered, and the ether evaporated under vacuo to obtain 0.47 g. (86% yield) of a viscous red liquid product that assayed 100% for 2,4,6-tri-(tert.-butylazo)-1,3,5-triazine by an iodometric titration. Its infrared spectrum was in accord with the proposed structure.

2,4,6-Tri-(tert.-butylazo)-1,3,5-triazine is a thermally sensitive free radical and gas generator that begins to evolve nitrogen slowly at 102° C. This product is also useful as an oxidizing agent as evidenced by the fact that it oxidized iodide ion to free iodine.

EXAMPLE XXII

Preparation of 2(-tert.-butylazo)propene

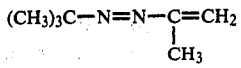

To a solution of 6.75 g. (0.077 m.) tert.-butylhydrazine in 50 ml. of methylene chloride containing 2 g. of anhydrous sodium sulfate, was added 3.0 g. (0.0326 m.) chloroacetone. The addition was carried out dropwise holding the reaction temperature below 10° C. with an ice bath. The reaction was stirred an additional 45 minutes and filtered. The filtrate was washed with cold water (10° C.), dried over anhydrous sodium sulfate, filtered and the methylene chloride evaporated off using a rotating evaporator and a 20° C. water bath. A yellow oil containing some solids suspended in it was obtained. The crude material was slurried in cold pentane and filtered. The pentane was then evaporated off from the filtrate on the rotating evaporator. The yield was 1.9 g. (47%) of a yellow oil. The infra-red spectrum was consistent with the structure of the proposed compound. 2-tert.-butylazopropene is a thermally unstable compound and evolves nitrogen at room temperature and is therefore a very low temperature blowing agent.

EXAMPLE XXIII

Preparation of 1(-tert.-butylazo)cyclohexene

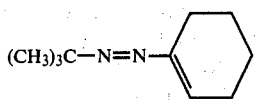

To a solution of 11 g. (0.125 m.) tert.-butylhydrazine in 80 ml. of methylene chloride containing 2 g. anhydrous sodium sulfate, was added 6.8 g. (0.052 m.) alpha-chlorocyclohexanone. The addition was carried out dropwise and the reaction temperature was maintained at 20° C.±5° by an ice bath. The solution immediately turned yellow, but the reaction was stirred for an additional 1 hour after the addition was complete before filtering it. The filtered methylene chloride solution was washed with 100 ml. water, dried over anhydrous sodium sulfate, filtered and the methylene chloride evaporated off. A viscous, gelatinous liquid remained. The material was cooled in the freezer and then filtered. A white solid, 0.1 g., remained on the filter. The filtrate weighed 8.4 g. (97% yield) and its infra-red spectrum was consistent with the proposed structure. It showed the absence of N-H and carbonyl bands and the presence of a carbon-carbon double bond (1650 cm$^{-1}$) and a conjugated azo bond (1510 cm$^{-1}$).

The product evolves nitrogen at 60° C.

1(-tert.-butylazo)cyclohexene gelled the unsaturated polyester-styrene resin of Example III at room temperature.

EXAMPLE XXIV

Preparation of 1-tert. butylazo-1-carbamylcyclohexane

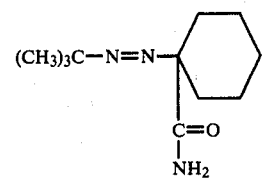

To 100 ml. of 95% H$_2$SO$_4$ in a 4 neck 250 ml. round bottom flask, cooled to −5° C. in a salt-ice bath, was added 23.0 g. (0.119 m.) of 1-tert. butylazo-1-cyanocyclohexene over a ½ hour period holding the temperature between −5° and 0° C. during the addition. The temperature was allowed to slowly rise to 20° C. over 1 hour, stirred 1 hour at 20° C. and finally stirred for 3 hours at 25° C. The acid solution was then added slowly to 750 ml. of rapidly stirred cold water, holding the temperature of the water between 10° and 15° C. The reaction was stirred ½ hour and filtered. The filter cake was washed acid free with water and dried. After drying it was slurried in 50 ml. pentane and filtered. The yield was 17.3 g. of a light yellow solid with a melting range of 86°–92° C. (91°–93° C. after recryst. from benzene-pentane). The percent yield was 69%. The pentane filtrate was stripped to dryness leaving 4.4 g. of unreacted starting material. The corrected percent yield was 85.5%. The infrared spectrum of the product was consistent with the structure of 1-t-butylazo-1-carbamylcyclohexane.

1-t-butylazo-1-carbamylcyclohexane is a thermally sensitive free radical and gas generator. It evolves nitrogen above 120° C. It cured the unsaturated-polyester-styrene resin of Example III at a 1.0 weight percent loading at 240° F. (115.6° C.) giving a peak exotherm of 444° F. (228.9° C.) in 6.8 minutes.

EXAMPLE XXV

Preparation of 2-t-butylazo-2-carbamylpropane

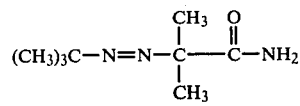

The method of preparing 2-t-butylazo-2-carbamylpropane from alpha(t-butylazo)-isobutyronitrile was the same as that used in example XXIV for the preparation of 1-t-butylazo-1-carbamylcyclohexane. The product was a white solid having a melting rage of 80°–82° C.

The infrared spectrum of the product was consistent with the structure of 2-t-butylazo-2-carbamylpropane.

2-t-butylazo-2-carbamylpropane is a thermally sensitive free radical and gas generator. It evolves nitrogen above 120° C. It cured the unsaturated-polyester-styrene resin of Example III at a 1.0 weight percent loading at 240° F. (115.6° C.) giving a peak exotherm of 442° F. (227.8° C.) in 5.7 mins.

EXAMPLE XXVI 1-t-butylsemicarbazide

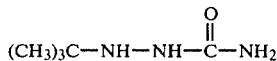

A. Urea Process

To a solution of 48 g. (0.386 m) tert.-butylhydrazine hydrochloride in 200 ml. water was added 72 g. (1.2 m) urea and the solution refluxed for 4 hours, cooled to 5° C. and filtered. The filter cake was recrystallized from 100 ml. water and dried. The yield was 42.3 g. (83.5%) of a white crystalline solid with a melting range of 200°-202° C. The infrared spectrum was in agreement with the structure of 1-t-butylsemicarbazide.

B. Cyanate Process

To a solution of 8.8 g. (0.1 m) t-butylhydrazine in 50 ml. water was added 50 ml. of an aqueous solution containing 8.1 g. (0.1 m) potassium cyanate. The mixture was stirred overnight, about 12 hours, at room temperature, about 25° C., cooled to 5° C. and filtered. The filter cake after drying weighed 11.6 g. (89%) and had a melting range of 203°-204° C. The infra-red spectrum was in agreement with the structure of 1-t-butylsemicarbazide.

EXAMPLE XXVII t-butylazoformamide

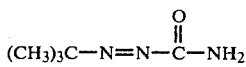

To a slurry of 5.0 g. (0.038 m) 1-t-butylsemicarbazide, 75 ml. methylene chloride, and 50 ml. saturated salt solution held at 5° C. by an ice bath was added 4.0 g. (0.025 m) potassium permanganate in small increments over 20 minutes. After the addition was complete, the reaction was stirred an additional ½ hour at 5°-10° C. and the methylene chloride layer separated. The aqueous layer was extracted with an additional 75 ml. methylene chloride, the methylene chloride layers combined, dried over anhydrous sodium sulfate, filtered and the methylene chloride evaporated off on a rotating evaporator. The yield was 4.9 g. (99%) of a yellow crystalline solid with a melting range of 103°-105° C. which assayed 100% by an iodometric titration. The infra-red spectrum is consistent with the structure of t-butylazoformamide.

EXAMPLE XXVIII

Polymerization of Ethyl Acrylate with α-tert-Butylazo-α-methyl-γ-carboxybutyronitrile and its Sodium Salt An emulsion containing 50 g. of deionized water, 40 g. ethyl acrylate, 4.8 g. Triton X-200, Rohm & Haas anionic surfactant, and 0.0769 g. ($3.65 \times 10^{-4}$ moles) α-tert-butylazo-α-methyl-γ-carboxy-butyronitrile (from Example X) was prepared. Approximately 25 g. of the emulsion was placed in a 250 ml. 4-neck round bottom flask equipped with a mechanical stirrer, thermometer and condenser. Nitrogen was passed through the system and the contents of the flask were heated to the reflux temperature of 82° C. When the temperature rose to 90° C., indicating polymerization was occurring, the balance of the emulsion was slowly added from a self-venting addition funnel, maintaining the temperature at 85°-87° C. At the end of the addition the temperature was raised to 95° C. for 5 minutes, a very small amount of hydroquinone added and the reaction cooled to room temperature. The total reaction time was 1⅓ hours. The final pH was 3.6. A 5 g. aliquot was weighed into a tared dish and the monomers and water evaporated and the conversion of monomer to polymer was determined to be 94%.

A similar polymerization was run under the same conditions using $3.65 \times 10^{-4}$ moles of the sodium salt of α-tert-butylazo-α-methyl-γ-carboxybutyronitrile as the initiator. The conversion was 92.3% and the final pH was 6.6.

A similar polymerisation ran under the same conditions for 3 hours with no initiator gave only 3½% conversion.

General procedures (GP) for the preparation of the compounds listed as Examples XXIX to L in Table 1 are set out below.

(GP 1) Preparation of t-Butylazo-α-chloro-alkanes and aralkanes of Examples XXIX to XXXIV Into a solution of 0.05 moles of the t-butylhydrazone of the appropriate ketone in 40 ml. of pentane in a 100 ml. flask, precooled to about −10° C. in an ice bath, was passed 0.025 moles of chlorine over 20 minutes. When the addition was complete, the reaction was stirred an additional ½ hour and the insoluble t-butylhydrazone hydrochloride filtered off. The pentane solution was washed with ice water to remove any residual hydrochloride, dried and the pentane removed on a rotating evaporator. Structure proofs were determined by infrared spectroscopy.

The t-butylhydrazone hydrochloride can be converted back to the t-butylhydrazone with sodium bicarbonate in water.

(GP 2) Preparation of t-Butylazo-α-methoxy-alkane and aralkanes of Examples XXXV to XL To a solution of 0.02 moles of 50% NaOH in 20 ml. of methanol, cooled to 5° C. in an ice bath, was added 0.015 moles of the desired t-butylazo-α-chloro compound over 5-10 minutes. The reaction was stirred an additional ½ hour and poured into 50 ml. cold water. The product was extracted out of the water with 50 ml. pentane. The solution was dried over anhydrous Na₂SO₄, filtered and the pentane evaporated. Structure proofs were determined by infrared spectroscopy.

(GP 3) Preparation of t-Butylazo-α-azido-alkanes and aralkanes of Examples XLI to XLV To a solution of 0.08 moles of sodium azide in 15 ml. water was added 76 ml. of acetone. The resulting mixture was cooled to 5° C. and 0.015 moles of the desired t-butylazo-α-chloro compound was added dropwise over 5-10 minutes. The reaction was stirred an additional ½ hour at 5° C. and poured into 150 ml water. The organic layer was extracted with pentane, dried over anhydrous Na$_2$SO$_4$, filtered and the pentane evaporated. Structure proofs were determined by infrared spectroscopy.

(GP 4) Preparation of t-Butylazo-α-t-butylperoxy-alkanes and aralkanes of Examples XLVI to L Into a solution of 2.0 g (0.05 m) of sodium hydroxide in 20 ml methanol at 5° C. was added 5.4 g (0.055 m) of 90.3% t-butylhydroperoxide and the solution stirred for 15 minutes. To this solution was added 0.04 moles of the desired t-butylazo-α-chloro-alkane over 5–10 minutes, holding the temperature at 5° C. with an ice bath. The reaction was stirred an additional ½ hour at 5° C. and poured into 100 ml water. The product was extracted with 50 ml pentane and the pentane solution washed with 50 ml of 10% KOH solution, water until neutral, dried over anhydrous sodium sulfate, filtered and the pentane evaporated off. Structure proofs were determined by infrared spectroscopy.

EXAMPLE LI

Preparation of 2-t-Butylazo-2-thiocyanato-4-methylpentane

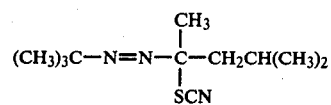

To a solution of 0.066 moles of sodium thiocyanate in 40 ml of 95% aqueous methanol, cooled to 5° C. in an ice bath was added 0.05 m of the t-butylazo-α-chloro compound of Example XXX over 5–10 minutes. The reaction mixture was stirred an additional ½ hour and poured into 400 ml water. The organic layer was extracted with 50 ml pentane, the pentane solution dried over anhydrius Na$_2$SO$_4$, filtered and the pentane evaporated. An infrared spectrum of the residue was in agreement with that of the desired product. Yield was 68%.

Table I

STRUCTURE $$(CH_3)_3C-N=N-\underset{Z}{\underset{|}{\overset{R_1}{\overset{|}{C}}}}-R_2$$

| EXAMPLE | NAME | Z | R$_1$ | R$_2$ | YIELD |
|---|---|---|---|---|---|
| XXIX | 1-t-butylazo-1-chlorocyclohexane | Cl | | —(CH$_2$)$_5$— | 52.5% |
| XXX | 2-t-butylazo-2-chloro-4-methylpentane | Cl | CH$_3$ | i-C$_4$H$_9$ | 98.7% |
| XXXI | 4-t-butylazo-4-chloro-2,6-dimethylheptane | Cl | i-C$_4$H$_9$ | i-C$_4$H$_9$ | 83.5% |
| XXXII | 2-t-butylazo-2-chloro-4-methyl-4-methoxypentane | Cl | CH$_3$ | —CH$_2$—C(CH$_3$)(OCH$_3$)—CH$_3$ | 54.5% |
| XXXIII | 1-t-butylazo-1-chloro-1-phenylethane | Cl | CH$_3$ | C$_6$H$_5$ | 76.0% |
| XXXIV | 2-t-butylazo-2-chloro-4,4-dimethylpentane | Cl | CH$_3$ | CH$_2$—C(CH$_3$)$_3$ | 64.5% |
| XXXV | 1-t-butylazo-1-methoxycyclohexane | OCH$_3$ | | —(CH$_2$)$_5$— | 63.0% |
| XXXVI | 2-t-butylazo-2-methoxy-4-methylpentane | OCH$_3$ | CH$_3$ | i-C$_4$H$_9$ | 48.0% |
| XXXVII | 4-t-butylazo-4-methoxy-2,6-dimethylheptane | OCH$_3$ | i-C$_4$H$_9$ | i-C$_4$H$_9$ | 76.0% |
| XXXVIII | 2-t-butylazo-4-methyl-2,4-dimethoxypentane | OCH$_3$ | CH$_3$ | —CH$_2$—C(CH$_3$)(OCH$_3$)—CH$_3$ | 67.0% |
| XXXIX | 1-t-butylazo-1-methoxy-1-phentylethane | OCH$_3$ | CH$_3$ | C$_6$H$_5$ | 88.0% |
| XL | 2-t-butylazo-2-methoxy-4,4-dimethylpentane | OCH$_3$ | CH$_3$ | —CH$_2$—C(CH$_3$)$_3$ | 80.0% |
| XLI | 1-t-butylazo-1-azidocyclohexane | N$_3$ | | —(CH$_2$)$_5$— | 83.0% |
| XLII | 2-t-butylazo-2-azido-4-methylpentane | N$_3$ | CH$_3$ | i-C$_4$H$_9$ | 83.0% |
| XLIII | 4-t-butylazo-4-azido-2,6-dimethylheptane | N$_3$ | i-C$_4$H$_9$ | i-C$_4$H$_9$ | 86.0% |
| XLIV | 2-t-butylazo-2-azido-4-methyl-4-methoxypentane | N$_3$ | CH$_3$ | —CH$_2$—C(CH$_3$)(OCH$_3$)—CH$_3$ | 61.0% |
| XLV | 1-t-butylazo-1-azido-1-phenylethane | N$_3$ | CH$_3$ | C$_6$H$_5$ | 96.0% |
| XLVI | 2-t-butylazo-2-t-butylperoxy-4-methylpentane | OOt-Bu | CH$_3$ | i-C$_4$H$_9$ | 75.0% |
| XLVII | 2-t-butylazo-2-t-butylperoxy-4-methyl-4-methoxypentane | OOt-Bu | CH$_3$ | —CH$_2$—C(OCH$_3$)(CH$_3$)—CH$_3$ | 55.0% |
| XLVIII | 2-butylazo-2-t-butylperoxy-4,4-dimethylpentane | OOt-Bu | CH$_3$ | —CH$_2$—C(CH$_3$)$_2$—CH$_3$ | 77.0% |
| XLIX | 1-t-butylazo-1-t-butylperoxy-cyclohexane | OOt-Bu | | —(CH$_2$)$_5$— | 65.0% |
| L | 1-t-butylazo-1-t-butylperoxy-1-phenylethane | OOt-Bu | CH$_3$ | C$_6$H$_5$ | 60.0% |

EXAMPLE LII

Preparation of
4-t-Butylazo-4-bromo-2,6-dimethylheptane

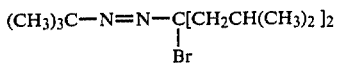

To a solution of 0.02 moles of the t-butylhydrazone of diisobutyl ketone in 25 ml pentane, cooled to 5° C. in an ice bath, was added 0.02 moles of bromine over 5 minutes. The reaction mixture was stirred an additional ½ hour at 5° C. and then filtered to remove any insoluble impurities. The pentane filtrate was dried over anhydrous Na$_2$SO$_4$, filtered and the pentane evaporated. An infrared spectrum of the residue was in agreement with that of the desired product. Yield was 40%.

EXAMPLE LIII

Preparation of 2-t-Butylazo-2-cyanato-4-methylpentane

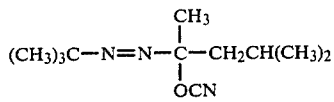

To a solution of 4.86 g (0.06 m) of potassium cyanate in 40 ml of 75% aqueous methanol, cooled to 5° C. in an ice bath, was added 0.034 moles of the t-butylazo-α-chloro compound of Example XXX. After the addition was complete the reaction was stirred for an additional ½ hour, poured into 400 ml water and the organic layer extracted with methylene chloride. The methylene chloride solution was dried over anhydrous sodium sulfate, filtered and the methylene chloride evaporated. An infrared spectrum of the residue was in agreement with that of the desired product. Yield was 74%.

EXAMPLE LIV

Preparation of
2-t-Butylazo-2-t-butoxy-4-methylpentane

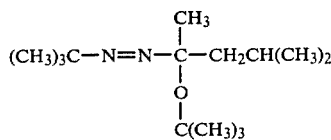

To a slurry of 0.025 moles of potassium t-butoxide in 50 ml of anhydrous t-butanol was added 0.02 moles of the t-butylazo-α-chloro compound of Example XXX. The temperature was held at 28° C. throughout the addition. After the addition was complete, the reaction was stirred for 20 minutes at 28° C. and poured into 200 ml water. The organic layer was extracted with pentane, the pentane solution washed twice with water, dried over anhydrous sodium sulfate, filtered and the pentane evaporated. An infrared spectrum of the residue was in agreement with that of the desired product. Yield was 68%.

EXAMPLE LV

Preparation of
2-t-Butylazo-2-propylthio-4-methylpentane

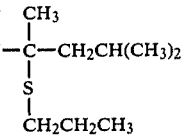

To a solution of 0.04 m of propylmercaptan and 0.05 m of NaOH in 30 ml of 80% aqueous ethanol was added over 20 minutes at 10° C., 0.02 moles of the t-butylazo-α-chloro compound of Example XXX. When the addition was complete the reaction was stirred for ½ hour, poured into 200 ml water and the organic layer extracted with pentane. After washing with water, the pentane solution was dried over anhydrous Na$_2$SO$_4$, filtered and the pentane evaporated. An infrared spectrum of the residue was in agreement with that of the desired product. Yield was 95%.

EXAMPLE LVI

Preparation of
2-(t-butylazo)-2-(benzoylperoxy)-4-methylpentane

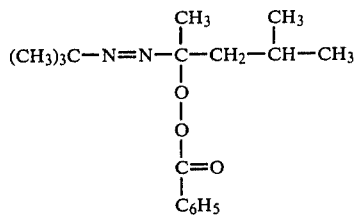

To a solution of 1.0 g (0.025 m) sodium hydroxide in 20 ml methanol, cooled to 5° C. in an ice bath, was added a slurry of 4.2 g (0.0275 m) of 90% perbenzoic acid. A very viscous slurry resulted. To this slurry was added 4.1 g of 2-t-butylazo-α-chloro-4-methylpentane keeping the temperature below 10° C. After the addition was complete, the reaction was stirred an additional 45 minutes and then poured into 150 ml of ice water. A small amount of solid formed and was removed by filtration. The product was extracted from the water with 30 ml pentane and the pentane solution washed with 10% KOH and then water until the washings were neutral. The pentane solution was dried over anhydrous Na$_2$SO$_4$, filtered and the pentane evaporated off leaving 4.1 g of a light yellow liquid. An infrared spectrum of the residue was in agreement with that of the desired product. The yield was 67%.

EXAMPLE LVII

Preparation of N,N'-Ethylene Bis(t-butylazoformamide)

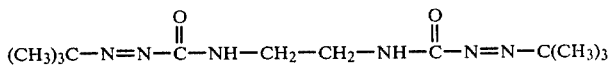

To a solution of 8 g (0.046 m) of isopropyl t-butylazocarboxylate in 25 ml ethanol, cooled to 5° C., was added 1.38 g (0.023 m) of ethylenediamine dropwise over 5 minutes. The temperature slowly rose to 12° and then subsided. The reaction was stirred an additional ½ hour and the ethanol stripped off. The resulting solid was slurried in warm benzene and filtered. The filter cake weighed 1.7 g and had a melting point of 166°–167° C. The infrared spectrum of the yellow solid was in agreement with that of the title product.

Evaporation of the benzene from the filtrate left 2.3 g of a yellow liquid whose infrared spectrum was in agreement with the structure of the mono product t-butylazo-N-(2-aminoethyl)formamide.

EXAMPLE LVIII

Preparation of Di[1-(t-butylazo)-1,3-dimethylbutyl]Peroxide

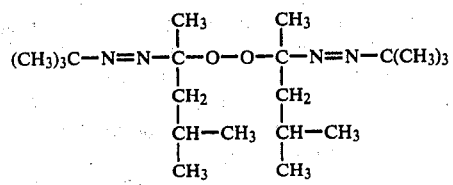

To a solution of 1.18 g. (0.0150 moles) of sodium peroxide in 30 ml. of 75% methanol cooled to 5° C. in a 50 ml. erlenmeyer flask was added 6.15 g. (0.03 moles) of 2-t-butylazo-2-chloro-4-methylpentane over 10 minutes. The reaction was stirred an additional 45 minutes and poured into 200 ml. of ice water. The organic layer was extracted with pentane, washed twice with 50 ml. saturated ammonium sulfate, once with 50 ml. water, saturated sodium bicarbonate solution and again with water. The pentane solution was dried with anhydrous sodium sulfate, filtered and stripped leaving 3.8 g. of a light yellow liquid (70% yield). The infrared spectrum was in agreement with that of the title compound. The product began to gas rapidly upon reaching room temperature.

EXAMPLE LIX

Preparation of 2-t-Butylazo-2-hydroxy-4-methylpentane

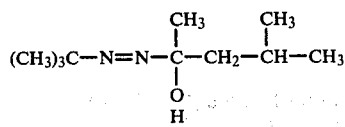

To a solution of 1.28 g. (0.016 moles) of 50% sodium hydroxide in 20 ml. water at 5° C. was added 3.2 g. (0.015 moles) of 2-t-butylazo-2-chloro-4-methylpentane dropwise over 10 minutes. The reaction was stirred an additional 4½ hours at 5° C. and extracted with 50 ml. of pentane. The pentane solution was washed twice with water, dried over anhydrous sodium sulfate, filtered and stripped leaving 2.6 g. of a light yellow liquid (90% yield). The infrared spectrum was in agreement with that of the title compound.

EXAMPLE LX

Preparation of 2-t-Butylazo-2-(propylamino)-4-methylpentane

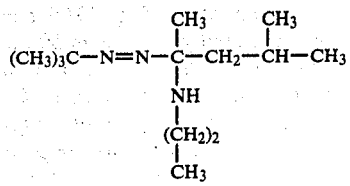

To a solution of 2.37 g. (0.04 moles) of n-propyl amine in 25 ml. of benzene was added 4.1 g. (0.02 moles) of b 2-t-butylazo-2-chloro-4-methylpentane. The reaction was stirred an additional 7½ hours at 5°–10° C. During this period there was a slow precipitation of n-propyl amine hydrochloride. The reaction was placed in the refrigerator overnight (15° C.). The next morning the n-propyl amine hydrochloride was filtered off and weighed (1.54 g. or 81% of theory). The filtrate was washed with cold water, dried over sodium sulfate, and the benzene removed at 10° C. on a rotating evaporator leaving 3.9 g. (86% yield) of a light yellow liquid which slowly evolves gas at room temperature. The infrared spectrum was in agreement with that of the title compound.

EXAMPLE LXI

Preparation of 4-t-Butylazo-2,4-dimethyloctane

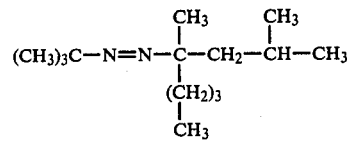

To a clean, dry, nitrogen purged 50 ml. round bottom 3 neck flask was transferred 25 ml. (1.4 g.=0.022 moles) of 9% butyllithium in a mixture of ⅓ pentane and ⅔ hexane by means of a hypodermic syringe. The flask and contents were cooled to 5° C. and a slow continuous passage of nitrogen was passed through the system. To the solution was added slowly 2.1 g. (0.01025 moles) of 2-t-butylazo-2-chloro-4-methylpentane in 10 ml. pentane from a pressure equalizing dropping funnel. After the addition was complete the reaction was stirred an additional 1 hour at 5° C. and the excess butyllithium destroyed by the slow addition of wet ether. The reaction mixture was then poured into 100 ml. H$_2$O and the organic layer separated. The organic layer was dried over sodium sulfate, filtered and the solvent removed on a rotating evaporator leaving 2.0 g. (93% yield) of a light yellow liquid. The infrared and ultraviolet spectra were in agreement with the structure of the title compound.

EXAMPLE LXII

Preparation of 2-t-Butylazo-2-phenyl-4-methylpentane

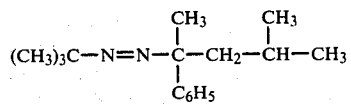

To a clean, dry 250 ml. round bottom 4 neck flask equipped with a magnetic stirrer, thermometer, condenser and addition funnel, which was being purged with nitrogen was added an ether solution containing 0.06 moles of phenyllithium. The solution was cooled to 5° C. and a solution of 10.25 g. (0.05 moles) of 2-t-butylazo-2-chloro-4-methylpentane in 50 ml. ether was added dropwise over ½ hour. After the addition was complete, the reaction was warmed to 20° C. and stirred for ½ hour. The excess phenyllithium was destroyed with wet ether and the reaction mixture poured into 200 ml. water. The ether layer was separated, dried over anhydrous sodium sulfate, filtered and the ether removed on a rotating evaporator leaving 11.9 g. (96%) of a liquid. The infrared spectrum was in agreement with the structure of the title compound.

EXAMPLE LXIII

Preparation of 1-t-Butylazo-1-phenylcyclohexane

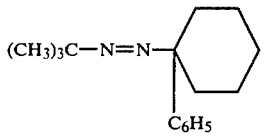

To a clean, dry 250 ml. round bottom 4 neck flask equipped with a magnetic stirrer, thermometer, condenser and addition funnel, which was being purged with nitrogen, was added an ether solution containing 0.06 moles of phenylmagnesium bromide. The solution was cooled to 5° C. and a solution of 8.7 g. (0.043 moles) of 1-t-butylazo-1-chlorocyclohexane in 50 ml. of ether was added dropwise over ½ hour. After the addition was complete, the reaction was stirred for 15 minutes at room temperature and the excess phenylmagnesium bromide destroyed by the addition of wet ether. The reaction mixture was poured into 200 ml. of cold water and the ether layer separated, washed with 5% HCl, saturated sodium bicarbonate solution, saturated sodium chloride solution, dried over anhydrous sodium sulfate, filtered and the ether removed on a rotating evaporator leaving 9.75 g. (93%) of a yellow liquid. The infrared spectrum of the product was in agreement with the structure of the title compound.

EXAMPLE LXIV

Preparation of 2-Phenyl-4-[1-(t-butylazo)-1,3-dimethylbutyl]-Δ²-1,3,4-oxadiazolin-5-one

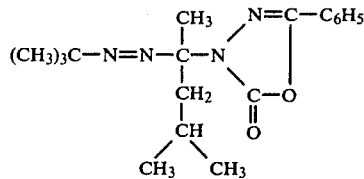

To a solution of 2.8 g. (0.026 moles) of 50% sodium hydroxide and 4.22 g. (0.026 moles) of 2-phenyl-Δ²-1,3,4-oxadiazolin-5-one in 30 ml. of methanol at 5° C. was added 5.14 g. (0.025 moles) of 2-t-butylazo-2-chloro-4-methylpentane dropwise over 10 minutes. After the addition was complete the reaction was stirred for an additional hour and poured into 200 ml. of water. The product was extracted with 50 ml. pentane, dried over anhydrous sodium sulfate, filtered, and the pentane removed on a rotating evaporator leaving 6.0 g. (73% yield) of dark yellow viscous liquid. The infrared spectrum of the product was in agreement with the structure of the title compound. Upon cooling the product crystallized and the material was purified by crystallizing it out of pentane at −30° C. The white crystals melt at 40° C.

EXAMPLE LXV

Preparation of 2,2,5,8,8,11,11,14,17,17-decamethyl-5,14-diisobutyl-Δ³,¹⁵-3,4,15,16-tetraaza-6,7,12,13-tetraoxaoctadecadiene

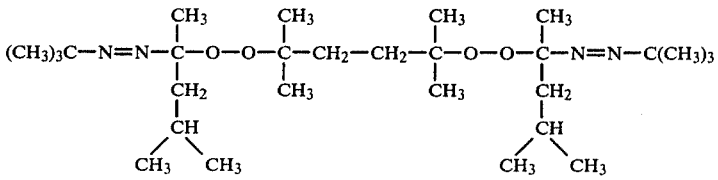

To a solution of 3.36 g. (0.042 moles) of 50% sodium hydroxide and 3.92 g. (0.022 moles) 2,5-dimethyl-2,5-dihydroperoxyhexane in 50 ml. of methanol at 5° C. was added 8.2 g. (0.04 moles) of 2-t-butylazo-2-chloro-4-methylpentane dropwise over 10 minutes. After the addition was complete, the reaction was stirred for 1 hour at 5°–10° C. and poured into 250 ml. ice water. The product was extracted with 50 ml. pentane, washed with cold 10% KOH, water, saturated sodium bicarbonate solution, water, dried over anhydrous sodium sulfate, filtered and the pentane removed at 10° C. on the rotating evaporator leaving 8.3 g. (80% yield) of a light yellow liquid which evolves nitrogen at 30° C. The infrared spectrum of the product is in agreement with the structure of the title compound.

EXAMPLE LXVI

Preparation of Diethyl
α-[1-(t-butylazo)-1,3-dimethylbutyl]malonate

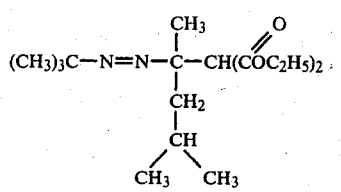

To a solution of 0.04 moles of sodium methoxide in 50 ml. methanol was slowly added 6.4 g. (0.04 moles) diethyl malonate and the reaction stirred 1 hour and cooled to 5° C. To the cooled solution was added 8.2 g. (0.04 moles) of 2-t-butylazo-2-chloro-4-methylpentane dropwise over 10 minutes. After the addition was complete, the reaction was stirred for an additional ½ hour and poured into 300 ml. cold water. The product was extracted with 100 ml. pentane, dried over anhydrous sodium sulfate, filtered and the pentane removed on a rotating evaporator leaving 9.8 g. (75% yield) of a yellow liquid. The infrared spectrum was in agreement with the structure of the title compound.

EXAMPLE LXVII

Reaction of the Sodium Salt of 2,4-Pentanedione with
2-t-Butylazo-2-chloro-4-methylpentane

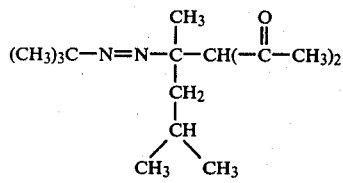
3-[1-(t-butylazo)-1,3-di-
methylbutyl]-2,4-pentanedione

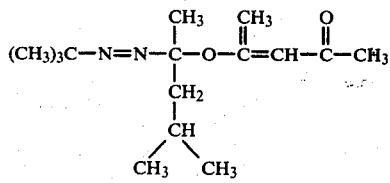
2,2,5,7-tetramethyl-5-iso-
butyl-Δ$^{3,7}$-3,4-disas-6-oxo-9-oxo-
decadiene To a solution of 0.03 moles of sodium methoxide in 40 ml. of methanol was added 3.6 g. (0.03 moles) of 2,4-pentanedione and the reaction stirred ½ hour and cooled to 5° C. To the cooled solution was added 6.15 g. (0.03 moles) of 2-t-butylazo-2-chloro-4-methylpentane dropwise over 10 minutes. After the addition was complete, the reaction was stirred an additional 1 hour and poured into 250 ml. of cold water. The product was extracted with pentane, dried over anhydrous sodium sulfate, filtered and the pentane removed on a rotating evaporator leaving 6.9 g. (86% yield) of a yellow liquid. The infrared spectrum of the product indicated that the product was a mixture of the above two isomeric structures.

EXAMPLE LXVIII

Preparation of
2-t-Butylazo-2-phenylhydrazo-4-methylpentane

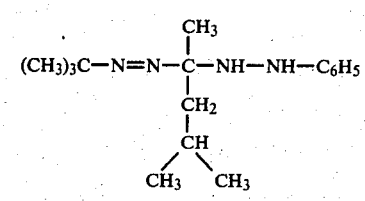

To a solution of 2.17 g. (0.02 moles) of phenylhydrazine in 25 ml. benzene, cooled to 5° C., was added 2.05 g. (0.01 mole) of 2-t-butylazo-2-chloro-4-methylpentane dropwise. After the addition was complete the reaction was stirred for 3 hours at 5°–10° C. and then placed in the refrigerator overnight (15° C.). The next morning the phenylhydrazine hydrochloride which had formed was filtered off, the benzene filtrate washed with water, dried over anhydrous sodium sulfate, filtered and the benzene removed on a rotating evaporator at 10° C. The product brownish-yellow liquid decomposes rapidly at room temperature. The infrared spectrum of the product was in agreement with the structure of the title compound.

EXAMPLE LXIX

Preparation of
2-t-Butylazo-2-t-butylhydrazo-4-methylpentane

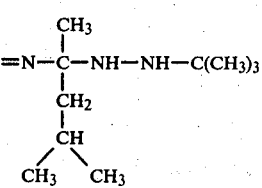

To a solution of 2.15 g. (0.02 moles) of 82% t-butylhydrazine in 25 ml. of benzene was added 2.05 g. (0.01 mole) of 2-t-butylazo-2-chloro-4-methylpentane holding the temperature at 5°–10° C. with an ice bath. The reaction was stirred an additional 3 hours and stored in the refrigerator (15° C.) overnight. The next morning the insoluble t-butylhydrazine hydrochloride which had formed was filtered off (1.0 g. or 84% of theory). The benzene filtrate was washed with water, dried over anhydrous sodium sulfate, filtered and the benzene removed at 10° C. on a rotating evaporator leaving 2.4 g. (94.5%) of a yellow liquid. The product evolves nitrogen at room temperature. The infrared spectrum of the product is in agreement with the structure of the title compound.

EXAMPLE LXX

Reaction of the Sodium Salt of 2-Nitroethane with 2-t-Butylazo-2-chloro-4-methylpentane

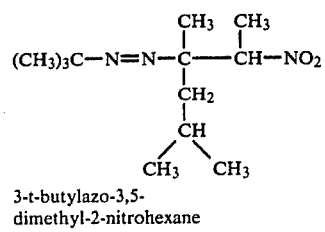

3-t-butylazo-3,5-dimethyl-2-nitrohexane

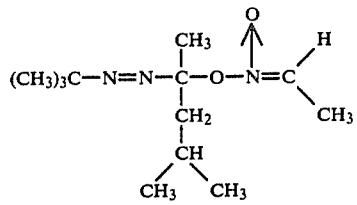

5,8,8-trimethyl-5-isobutyl-
$\Delta^{2,6}$-3,6,7-triaza-4-oxa-3-oxo-nonadiene

To a solution of 0.03 moles of sodium methoxide in 30 ml. of methanol was added dropwise 2.25 g. (0.03 moles) of nitroethane. The sodium salt which formed was insoluble in the methanol. The methanol slurry was cooled to 5° C. and 6.15 g. (0.03 moles) of 2-t-butylazo-2-chloro-4-methylpentane was slowly added to it holding the temperature at 5° C. with an ice bath. After the addition was complete, the reaction was stirred an additional hour at 5° C. and poured into 200 ml. of water. The organic layer was extracted with 50 ml. of pentane, dried over anhydrous sodium sulfate, filtered and the pentane removed on a rotating evaporator leaving 6.4 g. (87.6%) of a light yellow liquid which evolves nitrogen at room temperature. The infrared spectrum of the product indicated that the product was a mixture of the above two isomeric structures.

Thus having described the invention, what is claimed is.

1. A compound having the formula:

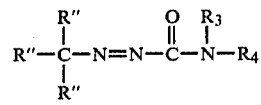

where:
(a) R" is alkyl of 1–13 carbons, phenyl, benzyl or phenethyl, not more than one R" being phenyl; and
(b) $R_3$ and $R_4$ are hydrogen, alkyl of 1–20 carbons, alkyl of 1–20 carbons containing a carboxy or methoxycarbonyl substituent, cycloalkyl of 3–6 carbons, or join to form alkylene of 2–16 carbons.

2. Claim 1 wherein (R")$_3$C- is t-butyl or t-cumyl.

3. Claim 1 wherein said compound is t-butylazoformamide.

* * * * *